(12) United States Patent
Karancsi et al.

(10) Patent No.: US 10,971,346 B2
(45) Date of Patent: Apr. 6, 2021

(54) LIQUID TRAP OR SEPARATOR FOR ELECTROSURGICAL APPLICATIONS

(71) Applicant: Micromass UK Limited, Wilmslow (GB)

(72) Inventors: Tamas Karancsi, Budapest (HU); Lajos Godorhazy, Erd (HU); Daniel Szalay, Budapest (HU); Zoltan Takats, Cambridge (GB); Julia Balog, Solymar (HU); Steven Derek Pringle, Darwen (GB); Daniel Simon, Morichida (HU)

(73) Assignee: Micromass UK Limited, Wilmslow (GB)

( * ) Notice: Subject to any disclaimer, the term of this patent is extended or adjusted under 35 U.S.C. 154(b) by 0 days.

(21) Appl. No.: 16/662,881

(22) Filed: Oct. 24, 2019

(65) Prior Publication Data

US 2020/0058478 A1   Feb. 20, 2020

Related U.S. Application Data

(63) Continuation of application No. 15/554,626, filed as application No. PCT/GB2016/050615 on Mar. 7, 2016, now Pat. No. 10,790,130.

(30) Foreign Application Priority Data

Mar. 6, 2015  (GB) .............................. GB1503863.1
Mar. 6, 2015  (GB) .............................. GB1503864.9
(Continued)

(51) Int. Cl.
*H01J 49/00*   (2006.01)
*H01J 49/04*   (2006.01)
(Continued)

(52) U.S. Cl.
CPC ............ *H01J 49/049* (2013.01); *A61B 1/041* (2013.01); *A61B 1/2736* (2013.01);
(Continued)

(58) Field of Classification Search
CPC ........ H01J 49/00; H01J 49/02; H01J 49/0027; H01J 49/0031; H01J 49/0404;
(Continued)

(56) References Cited

U.S. PATENT DOCUMENTS 5,696,352 A * 12/1997 Kourimsky .......... H01B 7/0009
                                                                174/126.3
5,800,597 A *  9/1998 Perrotta ................. B01D 46/24
                                                                 55/318
(Continued)

OTHER PUBLICATIONS

Partial European Search Report for EP20181905.9, dated Aug. 27, 2020, 14 pages.
(Continued)

*Primary Examiner* — Jason L McCormack
(74) *Attorney, Agent, or Firm* — Kacvinsky Daisak Bluni PLLC

(57) ABSTRACT

An apparatus for mass spectrometry and/or ion mobility spectrometry is disclosed comprising a first device arranged and adapted to generate aerosol, smoke or vapour from a target and one or more second devices arranged and adapted to aspirate aerosol, smoke, vapour and/or liquid to or towards an analyser. A liquid trap or separator is provided to capture and/or discard liquid aspirated by the one or more second devices.

18 Claims, 12 Drawing Sheets

(30) Foreign Application Priority Data

| Mar. 6, 2015 | (GB) | GB1503867.2 |
|---|---|---|
| Mar. 6, 2015 | (GB) | GB1503876.3 |
| Mar. 6, 2015 | (GB) | GB1503877.1 |
| Mar. 6, 2015 | (GB) | GB1503878.9 |
| Mar. 6, 2015 | (GB) | GB1503879.7 |
| Sep. 9, 2015 | (GB) | GB1516003.9 |
| Oct. 16, 2015 | (GB) | GB1518369.2 |

(51) Int. Cl.

| A61B 10/02 | (2006.01) |
|---|---|
| A61B 17/32 | (2006.01) |
| A61B 18/00 | (2006.01) |
| A61B 18/14 | (2006.01) |
| A61B 18/20 | (2006.01) |
| G01N 3/00 | (2006.01) |
| G01N 9/00 | (2006.01) |
| G01N 33/68 | (2006.01) |
| H01J 49/06 | (2006.01) |
| H01J 49/16 | (2006.01) |
| A61B 90/13 | (2016.01) |
| A61B 1/04 | (2006.01) |
| A61B 1/273 | (2006.01) |
| A61B 5/00 | (2006.01) |
| A61B 5/01 | (2006.01) |
| A61B 5/0507 | (2021.01) |
| A61B 5/055 | (2006.01) |
| A61B 6/03 | (2006.01) |
| A61B 8/13 | (2006.01) |
| A61B 10/00 | (2006.01) |
| A61B 17/00 | (2006.01) |
| A61B 18/04 | (2006.01) |
| A61B 18/18 | (2006.01) |
| A61F 13/38 | (2006.01) |
| C12Q 1/02 | (2006.01) |
| C12Q 1/04 | (2006.01) |
| C12Q 1/18 | (2006.01) |
| C12Q 1/24 | (2006.01) |
| G01N 1/22 | (2006.01) |
| G01N 27/622 | (2021.01) |
| G01N 27/624 | (2021.01) |
| G01N 30/72 | (2006.01) |
| G01N 33/487 | (2006.01) |
| G01N 33/92 | (2006.01) |
| H01J 49/02 | (2006.01) |
| H01J 49/10 | (2006.01) |
| H01J 49/14 | (2006.01) |
| H01J 49/24 | (2006.01) |
| H01J 49/26 | (2006.01) |
| G16B 20/00 | (2019.01) |
| G16H 70/00 | (2018.01) |
| G16H 20/00 | (2018.01) |
| G16H 10/40 | (2018.01) |
| G16H 15/00 | (2018.01) |
| G16H 50/20 | (2018.01) |
| A61B 1/00 | (2006.01) |
| A61B 1/31 | (2006.01) |
| A61B 5/145 | (2006.01) |
| G06F 19/00 | (2018.01) |

(52) U.S. Cl.
CPC .......... *A61B 5/0066* (2013.01); *A61B 5/0075* (2013.01); *A61B 5/015* (2013.01); *A61B 5/055* (2013.01); *A61B 5/0507* (2013.01); *A61B 6/032* (2013.01); *A61B 6/037* (2013.01); *A61B 8/13* (2013.01); *A61B 10/00* (2013.01); *A61B 10/0041* (2013.01); *A61B 10/0233* (2013.01); *A61B 10/0283* (2013.01); *A61B 17/00* (2013.01); *A61B 17/320068* (2013.01); *A61B 18/00* (2013.01); *A61B 18/04* (2013.01); *A61B 18/042* (2013.01); *A61B 18/14* (2013.01); *A61B 18/1445* (2013.01); *A61B 18/1815* (2013.01); *A61B 18/20* (2013.01); *A61B 90/13* (2016.02); *A61F 13/38* (2013.01); *C12Q 1/025* (2013.01); *C12Q 1/04* (2013.01); *C12Q 1/18* (2013.01); *C12Q 1/24* (2013.01); *G01N 1/2202* (2013.01); *G01N 3/00* (2013.01); *G01N 9/00* (2013.01); *G01N 27/622* (2013.01); *G01N 27/624* (2013.01); *G01N 30/724* (2013.01); *G01N 33/487* (2013.01); *G01N 33/6848* (2013.01); *G01N 33/6851* (2013.01); *G01N 33/92* (2013.01); *H01J 49/0004* (2013.01); *H01J 49/0027* (2013.01); *H01J 49/0031* (2013.01); *H01J 49/0036* (2013.01); *H01J 49/025* (2013.01); *H01J 49/0404* (2013.01); *H01J 49/044* (2013.01); *H01J 49/0422* (2013.01); *H01J 49/0445* (2013.01); *H01J 49/0463* (2013.01); *H01J 49/0468* (2013.01); *H01J 49/061* (2013.01); *H01J 49/068* (2013.01); *H01J 49/10* (2013.01); *H01J 49/14* (2013.01); *H01J 49/16* (2013.01); *H01J 49/164* (2013.01); *H01J 49/24* (2013.01); *H01J 49/26* (2013.01); *A61B 1/00013* (2013.01); *A61B 1/31* (2013.01); *A61B 5/14542* (2013.01); *A61B 2010/0083* (2013.01); *A61B 2017/320069* (2017.08); *A61B 2018/00577* (2013.01); *A61B 2018/00589* (2013.01); *A61B 2018/00994* (2013.01); *A61B 2218/002* (2013.01); *A61B 2218/008* (2013.01); *G01N 33/48735* (2013.01); *G01N 2001/2223* (2013.01); *G01N 2333/195* (2013.01); *G01N 2405/00* (2013.01); *G01N 2405/04* (2013.01); *G01N 2405/08* (2013.01); *G01N 2570/00* (2013.01); *G01N 2800/26* (2013.01); *G06F 19/324* (2013.01); *G16B 20/00* (2019.02); *G16H 10/40* (2018.01); *G16H 15/00* (2018.01); *G16H 20/00* (2018.01); *G16H 50/20* (2018.01); *G16H 70/00* (2018.01)

(58) Field of Classification Search
CPC ............... H01J 49/0409; H01J 49/0422; H01J 49/0463; H01J 49/0468; H01J 49/26; G01N 1/00; G01N 1/028; G01N 1/10; G01N 1/22; G01N 1/2202; G01N 1/2205; G01N 1/2214
USPC ........................................ 250/281, 282, 288
See application file for complete search history.

(56) References Cited

U.S. PATENT DOCUMENTS

| 5,969,352 | A | * | 10/1999 | French | H01J 49/105 250/288 |
|---|---|---|---|---|---|
| 7,960,711 | B1 | * | 6/2011 | Sheehan | H01J 49/045 250/493.1 |
| 2003/0042412 | A1 | * | 3/2003 | Park | H01J 49/0068 250/281 |
| 2005/0178975 | A1 | * | 8/2005 | Glukhoy | H01J 49/147 250/427 |
| 2006/0113463 | A1 | * | 6/2006 | Rossier | H01J 49/167 250/288 |

(56) References Cited

U.S. PATENT DOCUMENTS

| | | | |
|---|---|---|---|
| 2007/0114388 A1 | 5/2007 | Ogawa et al. | |
| 2007/0114394 A1* | 5/2007 | Combs | H01J 49/38 |
| | | | 250/292 |
| 2012/0048264 A1 | 3/2012 | Finlay et al. | |
| 2013/0181126 A1* | 7/2013 | Jong | G01N 15/10 |
| | | | 250/287 |
| 2014/0268134 A1 | 9/2014 | OConnor | |
| 2016/0341712 A1* | 11/2016 | Agar | G01N 33/57496 |

OTHER PUBLICATIONS

Roddy, T., et al., "Imaging of Freeze-Fractured Cells with in Situ Fluorescence and Time-of-Flight Secondary Ion Mass Spectrometry", Analytical Chemistry 74(16):4011-4019 (2002).

Petrotchenko, E.V., et al., "Combining Fluorescence Detection and Mass Spectrometric Analysis for Comprehensive and Quantitative Analysis of Redox-Sensitive Cysteines in Native Membrane Proteins", Analytical Chemistry 78 (23):7959-7966 (2006).

Ablonczy, Z., et al., "The utilization of fluorescence to identify the components of lipofuscin by imaging mass spectrometry", Proteomics 14(7-8):936-944.

Enthaler, B., et al., "Improved sample preparation for MALDI-MSI of endogenous compounds in skin tissue sections and mapping of exogenous active compounds subsequent to ex-vivo skin penetration" Anal Bioanal Chem 402:1159-1167 (2012).

Extended EP search report for EP Application No. 20172634.6, dated Sep. 14, 2020, 8 pages.

Examination Report for Indian Patent Application No. 201717035539, dated Jan. 27, 2021.

\* cited by examiner

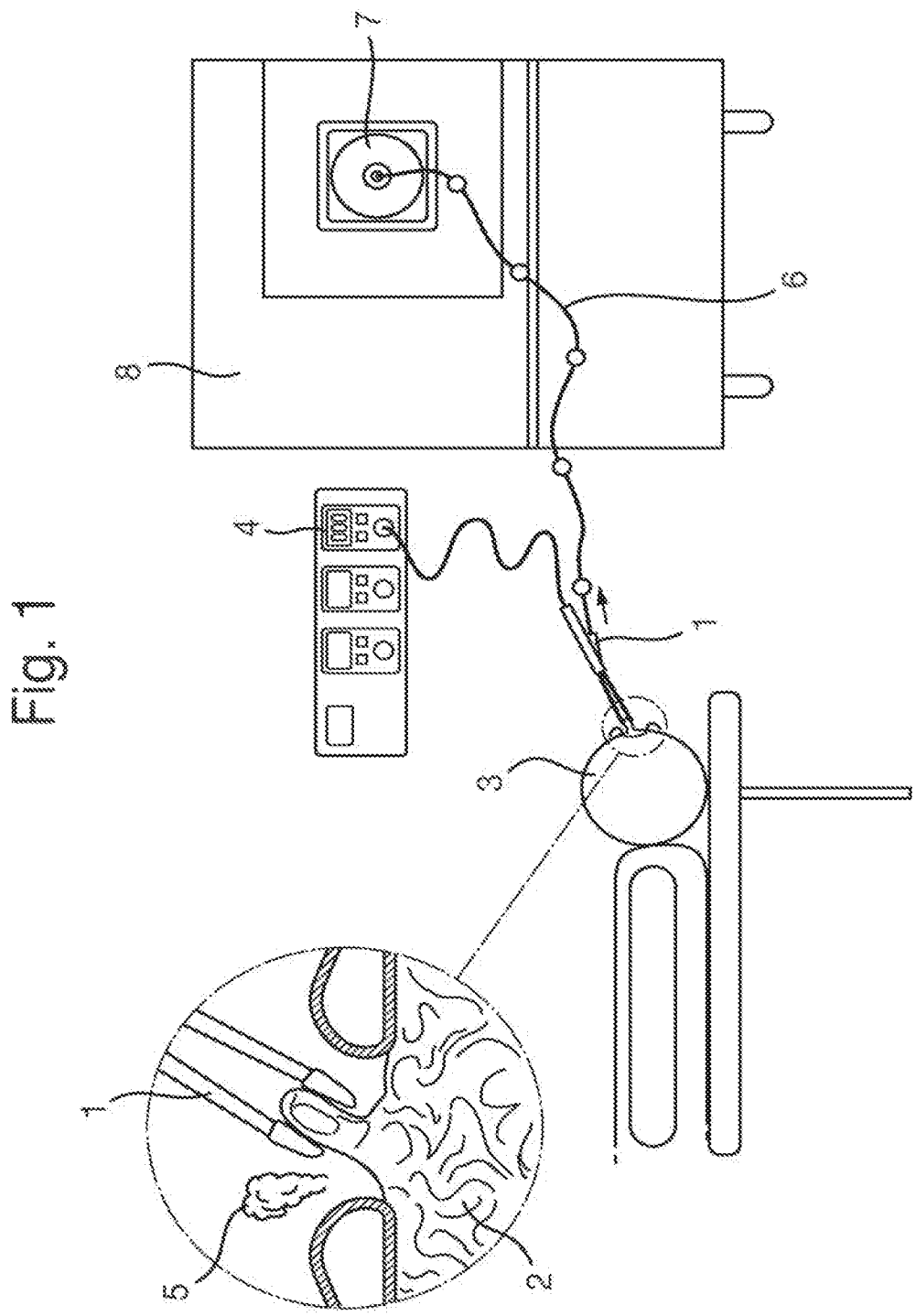

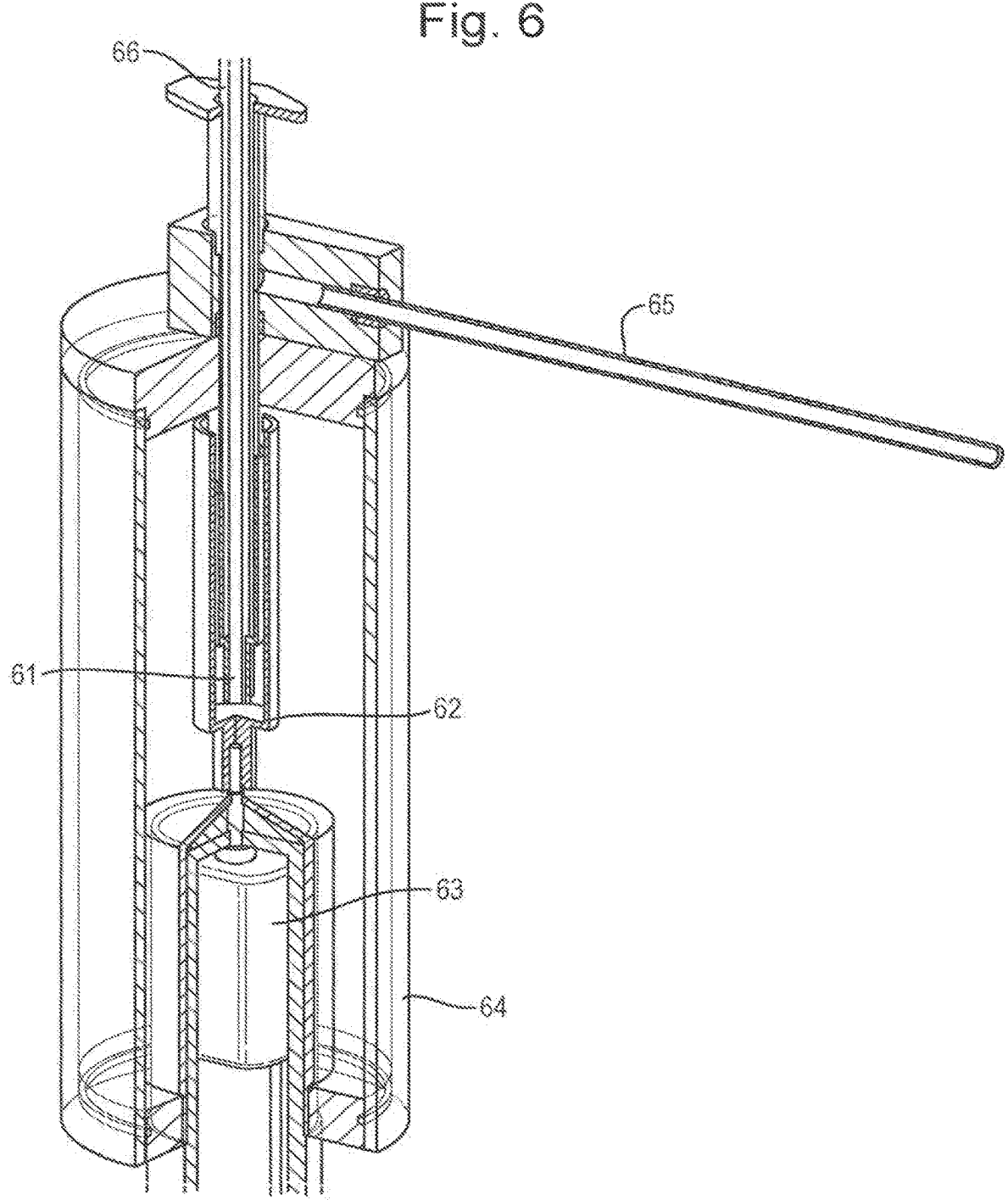

LIQUID TRAP OR SEPARATOR FOR ELECTROSURGICAL APPLICATIONS

CROSS-REFERENCE TO RELATED APPLICATIONS

This application is a continuation application of U.S. patent application Ser. No. 15/554,626, filed Aug. 30, 2017, which is the National Stage of International Application No. PCT/GB2016/050615, filed Mar. 7, 2016, which claims priority from and the benefit of United Kingdom patent application No. 1503876.3 filed on Mar. 6, 2015, United Kingdom patent application No. 1503864.9 filed on Mar. 6, 2015, United Kingdom patent application No. 1518369.2 filed on Oct. 16, 2015, United Kingdom patent application No. 1503877.1 filed on Mar. 6, 2015, United Kingdom patent application No. 1503867.2 filed on Mar. 6, 2015, United Kingdom patent application No. 1503863.1 filed on Mar. 6, 2015, United Kingdom patent application No. 1503878.9 filed on Mar. 6, 2015, United Kingdom patent application No. 1503879.7 filed on Mar. 6, 2015 and United Kingdom patent application No. 1516003.9 filed on Sep. 9, 2015. The entire contents of these applications are incorporated herein by reference.

FIELD OF THE INVENTION

The present invention generally relates to mass spectrometry and/or ion mobility spectrometry, and in particular to apparatus for performing ambient ionisation mass spectrometry and/or ion mobility spectrometry such as rapid evaporative ionisation mass spectrometry ("REIMS"), mass spectrometers, ion mobility spectrometers, methods of ambient ionisation mass spectrometry and/or ion mobility spectrometry such as rapid evaporative ionisation mass spectrometry, methods of mass spectrometry, methods of ion mobility spectrometry, methods of electrosurgery and an electrosurgical apparatus. Various embodiments are contemplated wherein analyte ions generated by an ambient ionisation ion source are then subjected either to: (i) mass analysis by a mass analyser or filter such as a quadrupole mass analyser or a Time of Flight mass analyser; (ii) ion mobility analysis (IMS) and/or differential ion mobility analysis (DMA) and/or Field Asymmetric Ion Mobility Spectrometry (FAIMS) analysis; and/or (iii) a combination of firstly ion mobility analysis (IMS) and/or differential ion mobility analysis (DMA) and/or Field Asymmetric Ion Mobility Spectrometry (FAIMS) analysis followed by secondly mass analysis by a mass analyser or filter such as a quadrupole mass analyser or a Time of Flight mass analyser (or vice versa). Various embodiments also relate to an ion mobility spectrometer and/or mass analyser and a method of ion mobility spectrometry and/or method of mass analysis.

BACKGROUND

Gastro-intestinal cancers are a leading cause of mortality and account for 23% of cancer-related deaths worldwide. In order to improve outcomes from these cancers, novel tissue characterisation methods are needed in order to facilitate accurate diagnosis.

Rapid evaporative ionisation mass spectrometry ("REIMS") may be used for the real time identification of tissues, e.g., during surgical interventions. Coupling of mass spectrometry with a surgical diathermy device has resulted in a sampling technology which has an intra-operative tissue identification accuracy of 92-100%.

This sampling technology allows surgeons to more efficiently resect tumours intra-operatively through minimizing the amount of healthy tissue removed whilst ensuring that all the cancerous tissue is removed.

Rapid evaporative ionisation mass spectrometry analysis of biological tissue has been shown to yield phospholipid profiles showing high histological and histopathological specificity similar to Matrix Assisted Laser Desorption Ionisation ("MALDI"), Secondary Ion Mass Spectrometry ("SIMS") and Desorption Electrospray Ionisation ("DESI") imaging. A mass and/or ion mobility spectrometric signal is obtained by subjecting the cellular biomass to alternating electric current at radiofrequency which causes localized Joule-heating and the disruption of cells along with desorption of charged and neutral particles. The resulting aerosol or surgical smoke is then transported to a mass spectrometer and/or ion mobility spectrometer for on-line mass and/or ion mobility spectrometric analysis.

The known rapid evaporative ionisation mass spectrometry technique is typically performed on external tissues or tissues accessed through surgery.

It is desired to provide an improved method of and apparatus for rapid evaporative ionisation mass spectrometry.

SUMMARY

According to an aspect there is provided apparatus for mass spectrometry and/or ion mobility spectrometry comprising:

a first device arranged and adapted to generate aerosol, smoke or vapour from a target;

one or more second devices arranged and adapted to aspirate aerosol, smoke, vapour and/or liquid to or towards an analyser for analysis; and a liquid trap or separator arranged and adapted to capture and/or discard liquid aspirated by the one or more second devices.

Various embodiments are directed to apparatus for mass and/or ion mobility spectrometry, and in particular apparatus for performing rapid evaporative ionisation mass spectrometry, that comprises a first device, such as an electrosurgical tool, which is arranged and adapted to generate aerosol, smoke (e.g. surgical smoke) or vapour from a target tissue or sample. The aerosol, smoke or vapour may be aspirated and transported to an analyser for analysis.

The first device may comprise or may form part of an endoscopic probe. Thus, in accordance with various embodiments, the apparatus may be used to perform mass and/or ion mobility spectrometric analysis, and in particular rapid evaporative ionisation mass spectrometry analysis, in or of an endoscopic environment, for example, for the treatment of gastro-intestinal cancers.

However, the Applicants have found that performing mass and/or ion mobility spectrometric analysis, and in particular rapid evaporative ionisation mass spectrometry analysis, in or of an endoscopic environment presents a number of challenges.

For example, endoscopic environments will typically be moist and this necessitates strategies to prevent liquid from reaching the analyser (or at least to reduce the amount of liquid reaching the analyser). This is because the liquid present in the endoscopic environment will not typically be related to the tissue sample of interest, and moreover, may damage the analyser.

However, the Applicants have found that strategies designed to reduce the amount of liquid that is initially aspirated, e.g. into the endoscopic probe, can have disadvantageous side effects on the operation of the device, and moreover, can often be ineffective because of the relatively closed environment in endoscopic sampling.

Accordingly, the Applicants have found that when performing mass and/or ion mobility spectrometric analysis, and in particular rapid evaporative ionisation mass spectrometry ("REIMS") or related analysis, in or of an endoscopic environment, in accordance with various embodiments it is beneficial to allow for the aspiration of undesired liquid, e.g. by the one or more second devices and/or endoscopic probe, and to then remove the undesired liquid to prevent the undesired liquid from reaching the analyser.

Thus, according to various embodiments a liquid trap or separator may be provided between the first device (e.g. electrosurgical tool) and the analyser. The liquid trap or separator may operate to capture and/or discard undesired liquid that may be aspirated, e.g. by the one or more second devices and/or endoscopic probe, together with the desired aerosol, surgical smoke or vapour generated during the analysis (e.g. rapid evaporative ionisation mass spectrometry ("REIMS") analysis), whilst still allowing the aerosol, surgical smoke or vapour to pass relatively uninhibited onwards to or towards the analyser. This beneficially prevents undesired liquid from reaching the analyser without affecting the measurement of the aerosol, smoke or vapour.

According to various embodiments the liquid trap or separator may be arranged, in use, to be external to the endoscopic environment, i.e. may not form part of the endoscopic probe. This means that the size of the endoscopic probe can beneficially be kept to a minimum, since it is not necessary to provide an additional means for preventing liquid from initially being aspirated by the endoscopic probe (or alternatively, at least the size of any such means can be minimised).

In addition, the apparatus may be arranged to have a minimal dead volume thus ensuring fast operation and minimal delay time, to avoid significant memory effects, to have a sufficient trapping volume in order to store the liquid aspirated, e.g., during a surgical intervention, to be easily cleanable and/or to be disposable, and to not modify the composition of the aerosol or surgical smoke and hence to not influence the measurement results.

Although particularly beneficial in the context of performing analysis of endoscopic environments, the apparatus according to various embodiments may also be useful in other situations. For example, there a number of applications of the apparatus according to various embodiments in which liquid that is unrelated to a target of interest (that is being analysed by the first device) may be aspirated to or towards the analyser. For example, in various embodiments, saline, blood, urine, mucus and/or other bodily fluids may be aspirated to or towards the analyser when analysing a target (e.g. tissue) of interest. Thus, according to various embodiments, the liquid trap or separator may capture and/or discard any one or more or all of these liquids in order to prevent the liquid reaching (and potentially damaging) the analyser.

It will be appreciated, therefore, that various embodiments provide an improved method of and apparatus for mass and/or ion mobility spectrometry.

The apparatus may comprise an endoscope.

The endoscope may comprise an endoscopic probe for probing an endoscopic environment.

The first device may comprise or form part of the endoscopic probe.

The first device may be arranged and adapted to be deployed through a port or opening in the endoscopic probe.

The endoscopic probe may comprise a tubing or a housing within which the first device may be located.

The tubing or housing may comprise a tool deployment opening optionally through which the first device may be deployed.

The first device may be at least partially retractable within the endoscopic probe, tubing or the housing.

The liquid trap or separator may not form part of or may be separate from the first device and/or the endoscopic probe.

The first device may comprise or form part of an ambient ion or ionisation source or the first device may generate the aerosol, smoke or vapour for subsequent ionisation by an ambient ion or ionisation source or other ionisation source.

The first device may comprise an electrosurgical device, a diathermy device, an ultrasonic device, hybrid ultrasonic electrosurgical device, surgical water jet device, hybrid electrosurgery, argon plasma coagulation device, hybrid argon plasma coagulation device and water jet device and/or a laser device.

The first device may comprise an ion source selected from the group consisting of: (i) a rapid evaporative ionisation mass spectrometry ("REIMS") ion source; (ii) a desorption electrospray ionisation ("DESI") ion source; (iii) a laser desorption ionisation ("LDI") ion source; (iv) a thermal desorption ion source; (v) a laser diode thermal desorption ("LDTD") ion source; (vi) a desorption electro-flow focusing ("DEFFI") ion source; (vii) a dielectric barrier discharge ("DBD") plasma ion source; (viii) an Atmospheric Solids Analysis Probe ("ASAP") ion source; (ix) an ultrasonic assisted spray ionisation ion source; (x) an easy ambient sonic-spray ionisation ("EASI") ion source; (xi) a desorption atmospheric pressure photoionisation ("DAPPI") ion source; (xii) a paperspray ("PS") ion source; (xiii) a jet desorption ionisation ("JeDI") ion source; (xiv) a touch spray ("TS") ion source; (xv) a nano-DESI ion source; (xvi) a laser ablation electrospray ("LAESI") ion source; (xvii) a direct analysis in real time ("DART") ion source; (xviii) a probe electrospray ionisation ("PESI") ion source; (xix) a solid-probe assisted electrospray ionisation ("SPA-ESI") ion source; (xx) a cavitron ultrasonic surgical aspirator ("CUSA") device; (xxi) a focussed or unfocussed ultrasonic ablation device; (xxii) a microwave resonance device; and (xxiii) a pulsed plasma RF dissection device.

The first device may comprise one or more electrodes, and the first device may be arranged and adapted to generate the aerosol, smoke or vapour from the target by contacting the target with the one or more electrodes.

The one or more electrodes may comprise a snare, optionally wherein the snare comprises a polypectomy snare.

The one or more electrodes may comprise one or more hooks, one or more grabbers, one or more blades, one or more knives, one or more serrated blades, one or more probes, one or more biopsy tools, one or more robotic tools, one or more pincers, one or more electrosurgical pencils, one or more forceps, one or more bipolar forceps, one or more coagulation devices, one or more irrigation devices and one or more imaging tools.

The one or more electrodes may comprise either: (i) a monopolar device, wherein the apparatus optionally further comprises a separate return electrode; (ii) a bipolar device; or (iii) a multi-phase RF device, wherein the apparatus optionally further comprises a separate return electrode or electrodes.

The one or more electrodes may comprise a rapid evaporation ionisation mass spectrometry ("REIMS") device.

The apparatus may comprise a device arranged and adapted to apply an AC or RF voltage to the one or more electrodes in order to generate the aerosol, smoke or vapour.

The device for applying the AC or RF voltage to the one or more electrodes may be arranged to apply one or more pulses of the AC or RF voltage to the one or more electrodes.

Application of the AC or RF voltage to the one or more electrodes may cause heat to be dissipated into the target.

The first device may comprise a laser for irradiating the target.

The first device may be arranged and adapted to generate aerosol, smoke or vapour from the target by direct evaporation or vaporisation of target material from the target by Joule heating or diathermy.

The first device may be arranged and adapted to direct ultrasonic energy into the target.

The aerosol may comprise uncharged aqueous droplets optionally comprising cellular material.

At least 50%, 55%, 60%, 65%, 70%, 75%, 80%, 85%, 90% or 95% of the mass or matter generated by the first device and which forms the aerosol may be in the form of droplets.

The first device may be arranged and adapted to generate aerosol wherein the Sauter mean diameter ("SMD", d32) of the aerosol is in a range: (i) <5 μm; (ii) 5-10 μm; (iii) 10-15 μm; (iv) 15-20 μm; (v) 20-25 μm; or (vi) >25 μm.

The aerosol may traverse a flow region with a Reynolds number (Re) in the range: (i) <2000; (ii) 2000-2500; (iii) 2500-3000; (iv) 3000-3500; (v) 3500-4000; or (vi) >4000.

Substantially at the point of generating the aerosol, the aerosol may comprise droplets having a Weber number (We) selected from the group consisting of: (i) <50; (ii) 50-100; (iii) 100-150; (iv) 150-200; (v) 200-250; (vi) 250-300; (vii) 300-350; (viii) 350-400; (ix) 400-450; (x) 450-500; (xi) 500-550; (xii) 550-600; (xiii) 600-650; (xiv) 650-700; (xv) 700-750; (xvi) 750-800; (xvii) 800-850; (xviii) 850-900; (xix) 900-950; (xx) 950-1000; and (xxi) >1000.

Substantially at the point of generating the aerosol, the aerosol may comprise droplets having a Stokes number ($S_k$) in the range: (i) 1-5; (ii) 5-10; (iii) 10-15; (iv) 15-20; (v) 20-25; (vi) 25-30; (vii) 30-35; (viii) 35-40; (ix) 40-45; (x) 45-50; and (xi) >50.

Substantially at the point of generating the aerosol, the aerosol may comprise droplets having a mean axial velocity selected from the group consisting of: (i) <20 m/s; (ii) 20-30 m/s; (iii) 30-40 m/s; (iv) 40-50 m/s; (v) 50-60 m/s; (vi) 60-70 m/s; (vii) 70-80 m/s; (viii) 80-90 m/s; (ix) 90-100 m/s; (x) 100-110 m/s; (xi) 110-120 m/s; (xii) 120-130 m/s; (xiii) 130-140 m/s; (xiv) 140-150 m/s; and (xv) >150 m/s.

The target may comprise native or unmodified target material.

The target may comprise biological tissue, biological matter, a bacterial colony or a fungal colony.

The biological tissue may comprise human tissue or non-human animal tissue.

The biological tissue may comprise in vivo biological tissue.

The biological tissue may comprise adrenal gland tissue, appendix tissue, bladder tissue, bone, bowel tissue, brain tissue, breast tissue, bronchi, coronal tissue, ear tissue, oesophagus tissue, eye tissue, gall bladder tissue, genital tissue, heart tissue, hypothalamus tissue, kidney tissue, large intestine tissue, intestinal tissue, larynx tissue, liver tissue, lung tissue, lymph nodes, mouth tissue, nose tissue, pancreatic tissue, parathyroid gland tissue, pituitary gland tissue, prostate tissue, rectal tissue, salivary gland tissue, skeletal muscle tissue, skin tissue, small intestine tissue, spinal cord, spleen tissue, stomach tissue, thymus gland tissue, trachea tissue, thyroid tissue, ureter tissue, urethra tissue, soft and connective tissue, peritoneal tissue, blood vessel tissue and/or fat tissue; (ii) grade I, grade II, grade III or grade IV cancerous tissue; (iii) metastatic cancerous tissue; (iv) mixed grade cancerous tissue; (v) a sub-grade cancerous tissue; (vi) healthy or normal tissue; or (vii) cancerous or abnormal tissue.

The first device may comprise a point of care ("POC"), diagnostic or surgical device.

The one or more second devices may be further arranged and adapted to transport the aspirated aerosol, smoke or vapour and/or liquid to or towards the analyser.

The one or more second devices may be arranged and adapted to transport the aspirated aerosol, smoke or vapour and/or liquid to or towards the analyser via the liquid trap or separator.

The apparatus may further comprise one or more tubes or flow lines, wherein the one or more second devices may be arranged and adapted to transport the aspirated aerosol, smoke or vapour and/or liquid through one or more tubes or flow lines.

The one or more tubes or flow lines may connect the first device to the liquid trap or separator and/or connect the first device to the analyser.

The one or more tubes or flow lines may comprise: (i) one or more first tubes or flow lines that connect the first device to the liquid trap or separator; and (ii) one or more second tubes or flow lines that connect the liquid trap or separator to the analyser.

The one or more second devices may be arranged and adapted to aspirate the aerosol, smoke or vapour and/or liquid through one or more fenestrations or aspiration ports.

The endoscopic probe may comprise the one or more fenestrations or aspiration ports.

The one or more second devices may comprise one or more pumps arranged and adapted to cause the aerosol, smoke or vapour and/or liquid to be aspirated and/or transported to or towards the analyser.

The liquid trap or separator may comprise a liquid detector arranged and adapted to detect aspirated liquid.

The liquid trap or separator may be arranged and adapted such that when the liquid detector detects aspirated liquid then the liquid trap or separator may be further arranged and adapted to capture and/or discard at least some of the liquid.

The liquid trap or separator may comprise a liquid collector or drain.

The liquid trap or separator may be arranged and adapted such that when the liquid detector detects aspirated liquid then the liquid trap or separator may be further arranged and adapted to divert at least some of the liquid to the liquid collector or drain.

The liquid detector may comprise an optical transmission detector, an optical reflection detector, an ultrasonic transmission detector, an ultrasonic reflectance detector, and/or an electrical detector.

The electrical detector may be arranged and adapted to measure the electrical conductivity and/or resistance of a section of the one or more tubes or flow lines.

The electrical detector may be arranged and adapted to measure the capacitance between two or more electrodes provided in a section of the one or more tubes or flow lines.

The ultrasonic transmission detector and/or the ultrasonic reflectance detector may comprise one or more ultrasonic transmitter and detector pairs.

The ultrasonic transmission detector and/or the ultrasonic reflectance detector may be arranged and adapted to detect aspirated liquid by detecting changes in an ultrasonic signal due to aspirated liquid absorbing ultrasonic energy.

The liquid trap or separator may comprise one or more porous and/or absorbent materials arranged and adapted to absorb and/or capture and/or discard aspirated liquid.

The liquid trap or separator may comprise one or more tubes or flow lines formed at least in part from one or more porous and/or absorbent materials.

The liquid trap or separator may be arranged and adapted to pass the aerosol, smoke or vapour and/or liquid through the one or more tubes or flow lines formed at least in part from the one or more porous and/or absorbent materials.

The liquid trap or separator may comprise a centrifugal liquid separator.

The liquid trap or separator may comprise a sealed chamber comprising an inlet, and the liquid trap or separator may be arranged and adapted such that in use the aerosol, smoke or vapour and/or liquid is introduced into the chamber though the inlet.

The sealed chamber may comprise an outlet, and the liquid trap or separator may be arranged and adapted such that in use aerosol, smoke and/or vapour can leave the chamber through the outlet substantially without liquid leaving the chamber.

In use an exit of the inlet may be located below an entrance of the outlet.

The apparatus may comprise a device which is arranged and adapted to generate feedback and/or an alarm and/or an alert to a user of the apparatus when the liquid trap or separator contains liquid at or close to a maximum level.

The apparatus may comprise a device which is arranged and adapted to reduce or stop electrical power to or otherwise disable the apparatus in the event that the liquid trap or separator contains liquid at or close to a maximum level.

The liquid may comprise water, saliva, digestive fluids, chyme, saline, blood, urine, mucus and/or one or more other bodily fluids.

According to an aspect there is provided a mass and/or ion mobility spectrometer comprising apparatus as described above.

The mass and/or ion mobility spectrometer may be arranged and adapted to pass the aerosol, smoke and/or vapour into a vacuum chamber of the mass and/or ion mobility spectrometer.

The mass and/or ion mobility spectrometer may comprise an ionisation device arranged and adapted to ionise the aerosol, smoke and/or vapour to form analyte ions.

The ionisation device may comprise a collision surface located within a vacuum chamber of the mass and/or ion mobility spectrometer.

The mass and/or ion mobility spectrometer may be arranged and adapted to cause at least some of the aerosol, smoke and/or vapour to impact upon the collision surface in order to form the analyte ions.

The mass and/or ion mobility spectrometer may comprise a heating device which is arranged and adapted to heat the collision surface.

The heating device may be arranged and adapted to heat the collision surface to a temperature selected from the group consisting of: (i) about <100° C.; (ii) about 100-200° C.; (iii) about 200-300° C.; (iv) about 300-400° C.; (v) about 400-500° C.; (vi) about 500-600° C.; (vii) about 600-700° C.; (viii) about 700-800° C.; (ix) about 800-900° C.; (x) about 900-1000° C.; (xi) about 1000-1100° C.; and (xii) about >1100° C.

The mass and/or ion mobility spectrometer may comprise a device arranged and adapted to add a matrix to the aerosol, smoke and/or vapour.

The matrix may be added, in use, to the aerosol, smoke and/or vapour prior to the aerosol, smoke and/or vapour impacting upon the collision surface.

The matrix may be selected from the group consisting of: (i) a solvent for the aerosol, smoke and/or vapour; (ii) an organic solvent; (iii) a volatile compound; (iv) polar molecules; (v) water; (vi) one or more alcohols; (vii) methanol; (viii) ethanol; (ix) isopropanol; (x) acetone; and (xi) acetonitrile.

The matrix may comprise a lockmass, lock mobility or calibration compound.

The mass and/or ion mobility spectrometer may comprise the analyser which may be arranged and adapted to analyse the aerosol, smoke, vapour and/or the analyte ions.

The analyser may comprise: (i) a mass analyser and/or ion mobility analyser for mass analysing and/or ion mobility analysing the aerosol, smoke, vapour, or the analyte ions and/or ions derived from the aerosol, smoke, vapour, the analyte ions; (ii) an ion mobility device for determining the ion mobility, collision cross section or interaction cross section of the aerosol, smoke, vapour, or the analyte ions and/or ions derived from the aerosol, smoke, vapour, the analyte ions; and/or (iii) one or more fragmentation, collision or reaction devices for fragmenting or reacting the aerosol, smoke, vapour, or the analyte ions.

Various embodiments are contemplated wherein analyte ions generated by the ambient ionisation ion source are then subjected either to: (i) mass analysis by a mass analyser or filter such as a quadrupole mass analyser or a Time of Flight mass analyser; (ii) ion mobility analysis (IMS) and/or differential ion mobility analysis (DMA) and/or Field Asymmetric Ion Mobility Spectrometry (FAIMS) analysis; and/or (iii) a combination of firstly ion mobility analysis (IMS) and/or differential ion mobility analysis (DMA) and/or Field Asymmetric Ion Mobility Spectrometry (FAIMS) analysis followed by secondly mass analysis by a mass analyser or filter such as a quadrupole mass analyser or a Time of Flight mass analyser (or vice versa). Various embodiments also relate to an ion mobility spectrometer and/or mass analyser and a method of ion mobility spectrometry and/or method of mass analysis.

The mass and/or ion mobility spectrometer may comprise a device which is arranged and adapted to provide real time and/or delayed information to a user of the first device.

The information may comprise mass and/or ion mobility spectral information and/or tissue classification information.

The mass and/or ion mobility spectrometer may comprise a device which is arranged and adapted to generate feedback and/or an alarm and/or an alert to a user of the first device when tissue or other matter from an undesired target region or area is being analysed.

The mass and/or ion mobility spectrometer may comprise a device which is arranged and adapted to reduce or stop electrical power to or otherwise disable the first device in the event that tissue or other matter from an undesired target region or area is being analysed.

The mass and/or ion mobility spectrometer may comprise a device which is arranged and adapted to generate feedback and/or an alarm and/or an alert to a user of the first device when the first device is operating in and/or is located in an undesired target region or area.

The mass and/or ion mobility spectrometer may comprise a device which is arranged and adapted to reduce or stop electrical power to or otherwise disable the first device in the event that the first device is operating in and/or is located in an undesired target region or area.

According to an aspect there is provided a method of mass spectrometry and/or ion mobility spectrometry comprising:

generating aerosol, smoke or vapour from a target using a first device;

aspirating aerosol, smoke or vapour and/or liquid to or towards an analyser; and capturing and/or discarding liquid aspirated by the one or more second devices using a liquid trap or separator.

The method may comprise providing an endoscope.

The endoscope may comprise an endoscopic probe.

The first device may comprise or form part of the endoscopic probe.

The endoscopic probed may comprise a tubing or a housing within which the first device may be located.

The tubing or housing may comprise a tool deployment opening and the first device may be deployed through the opening.

The first device may be at least partially retracted within and/or extended from the endoscopic probe, tubing or the housing.

The method may comprise inserting the endoscopic probe into an endoscopic environment.

The method may comprise deploying the first device through a port in the endoscopic probe.

The method may comprise generating the aerosol, smoke or vapour inside the endoscopic environment.

The liquid trap or separator may not form part of or may be separate from the first device and/or the endoscopic probe.

The first device may comprise an electrosurgical device, a diathermy device, an ultrasonic device, hybrid ultrasonic electrosurgical device, surgical water jet device, hybrid electrosurgery, argon plasma coagulation device, hybrid argon plasma coagulation device and water jet device and/or a laser device.

The first device may comprise or form part of an ambient ion or ionisation source or the first device may generate the aerosol, smoke or vapour for subsequent ionisation by an ambient ion or ionisation source or other ionisation source.

The first device may comprise an ion source selected from the group consisting of: (i) a rapid evaporative ionisation mass spectrometry ("REIMS") ion source; (ii) a desorption electrospray ionisation ("DESI") ion source; (iii) a laser desorption ionisation ("LDI") ion source; (iv) a thermal desorption ion source; (v) a laser diode thermal desorption ("LDTD") ion source; (vi) a desorption electro-flow focusing ("DEFFI") ion source; (vii) a dielectric barrier discharge ("DBD") plasma ion source; (viii) an Atmospheric Solids Analysis Probe ("ASAP") ion source; (ix) an ultrasonic assisted spray ionisation ion source; (x) an easy ambient sonic-spray ionisation ("EASI") ion source; (xi) a desorption atmospheric pressure photoionisation ("DAPPI") ion source; (xii) a paperspray ("PS") ion source; (xiii) a jet desorption ionisation ("JeDI") ion source; (xiv) a touch spray ("TS") ion source; (xv) a nano-DESI ion source; (xvi) a laser ablation electrospray ("LAESI") ion source; (xvii) a direct analysis in real time ("DART") ion source; (xviii) a probe electrospray ionisation ("PESI") ion source; (xix) a solid-probe assisted electrospray ionisation ("SPA-ESI") ion source; (xx) a cavitron ultrasonic surgical aspirator ("CUSA") device; (xxi) a focussed or unfocussed ultrasonic ablation device; (xxii) a microwave resonance device; and (xxiii) a pulsed plasma RF dissection device.

The step of generating aerosol, smoke or vapour from the target may comprise contacting the target with one or more electrodes.

The one or more electrodes may comprise a snare, optionally wherein the snare comprises a polypectomy snare.

The one or more electrodes may comprise one or more hooks, one or more grabbers, one or more blades, one or more knives, one or more serrated blades, one or more probes, one or more biopsy tools, one or more robotic tools, one or more pincers, one or more electrosurgical pencils, one or more forceps, one or more bipolar forceps, one or more coagulation devices, one or more irrigation devices and one or more imaging tools.

The one or more electrodes may comprise either: (i) a monopolar device, wherein the method optionally further comprises providing a separate return electrode; (ii) a bipolar device; or (iii) a multi-phase RF device, wherein the method optionally further comprises providing a separate return electrode or electrodes.

The one or more electrodes may comprise a rapid evaporation ionisation mass spectrometry ("REIMS") device.

The method may comprise applying an AC or RF voltage to the one or more electrodes in order to generate the aerosol, smoke or vapour.

The step of applying the AC or RF voltage to the one or more electrodes may comprise applying one or more pulses of the AC or RF voltage to the one or more electrodes.

The step of applying the AC or RF voltage to the one or more electrodes may cause heat to be dissipated into the target The step of generating aerosol, smoke or vapour from the target may comprise irradiating the target with a laser.

The step of generating aerosol, smoke or vapour may comprise generating the aerosol, smoke or vapour from the target by direct evaporation or vaporisation of target material from the target by Joule heating or diathermy.

The step of generating aerosol, smoke or vapour from the target may comprise directing ultrasonic energy into the target.

The aerosol may comprise uncharged aqueous droplets optionally comprising cellular material.

At least 50%, 55%, 60%, 65%, 70%, 75%, 80%, 85%, 90% or 95% of the mass or matter generated by the first device and which forms the aerosol may be in the form of droplets.

The step of generating aerosol may comprise generating aerosol wherein the Sauter mean diameter ("SMD", d32) of the aerosol is in a range: (i) <5 µm; (ii) 5-10 µm; (iii) 10-15 µm; (iv) 15-20 µm; (v) 20-25 µm; or (vi) >25 µm.

The aerosol may traverse a flow region with a Reynolds number (Re) in the range: (i) <2000; (ii) 2000-2500; (iii) 2500-3000; (iv) 3000-3500; (v) 3500-4000; or (vi) >4000.

Substantially at the point of generating the aerosol, the aerosol may comprise droplets having a Weber number (We) selected from the group consisting of: (i) <50; (ii) 50-100; (iii) 100-150; (iv) 150-200; (v) 200-250; (vi) 250-300; (vii) 300-350; (viii) 350-400; (ix) 400-450; (x) 450-500; (xi) 500-550; (xii) 550-600; (xiii) 600-650; (xiv) 650-700; (xv) 700-750; (xvi) 750-800; (xvii) 800-850; (xviii) 850-900; (xix) 900-950; (xx) 950-1000; and (xxi) >1000.

Substantially at the point of generating the aerosol, the aerosol may comprise droplets having a Stokes number ($S_k$) in the range: (i) 1-5; (ii) 5-10; (iii) 10-15; (iv) 15-20; (v) 20-25; (vi) 25-30; (vii) 30-35; (viii) 35-40; (ix) 40-45; (x) 45-50; and (xi) >50.

Substantially at the point of generating the aerosol, the aerosol may comprise droplets having a mean axial velocity selected from the group consisting of: (i) <20 m/s; (ii) 20-30 m/s; (iii) 30-40 m/s; (iv) 40-50 m/s; (v) 50-60 m/s; (vi) 60-70 m/s; (vii) 70-80 m/s; (viii) 80-90 m/s; (ix) 90-100 m/s; (x) 100-110 m/s; (xi) 110-120 m/s; (xii) 120-130 m/s; (xiii) 130-140 m/s; (xiv) 140-150 m/s; and (xv) >150 m/s.

The target may comprise native or unmodified target material.

The target may comprise biological tissue, biological matter, a bacterial colony or a fungal colony.

The biological tissue may comprise human tissue or non-human animal tissue.

The biological tissue may comprise in vivo biological tissue.

The biological tissue may comprise bladder tissue, bowel tissue, bronchi, esophagus tissue, genital tissue, large intestine tissue, intestinal tissue, larynx tissue, lung tissue, mouth tissue, nose tissue, prostate tissue, rectal tissue, small intestine tissue, stomach tissue, trachea tissue, ureter tissue, urethra tissue, soft and connective tissue, peritoneal tissue, blood vessel tissue and/or fat tissue; (ii) grade I, grade II, grade III or grade IV cancerous tissue; (iii) metastatic cancerous tissue; (iv) mixed grade cancerous tissue; (v) a sub-grade cancerous tissue; (vi) healthy or normal tissue; or (vii) cancerous or abnormal tissue.

The method may comprise a point of care ("POC"), diagnostic or surgical method.

The method may comprise transporting the aspirated aerosol, smoke or vapour and/or liquid to or towards the analyser.

The method may comprise transporting the aspirated aerosol, smoke or vapour and/or liquid to or towards the analyser via the liquid trap or separator.

The method may comprise transporting the aspirated aerosol, smoke or vapour and/or liquid through one or more tubes or flow lines.

The one or more tubes or flow lines may connect the first device to the liquid trap or separator and/or connect the first device to the analyser.

The one or more tubes or flow lines may comprise: (i) one or more first tubes or flow lines that connect the first device to the liquid trap or separator; and (ii) one or more second tubes or flow lines that connect the liquid trap or separator to the analyser.

The method may comprise aspirating the aerosol, smoke or vapour and/or liquid through one or more fenestrations or aspiration ports.

The endoscopic probe may comprise the one or more fenestrations or aspiration ports.

The method may comprise detecting aspirated liquid using a liquid detector. The method may comprise capturing and/or discarding at least some of the aspirated liquid when aspirated liquid is detected.

The liquid trap or separator may comprise a liquid collector or drain.

The method may comprise diverting at least some of the liquid to the liquid collector or drain when aspirated liquid is detected.

The liquid detector may comprise an optical transmission detector, an optical reflection detector, an ultrasonic transmission detector, an ultrasonic reflectance detector, and/or an electrical detector.

The method may comprise using the electrical detector to measure the electrical conductivity and/or resistance of a section of the one or more tubes or flow lines.

The method may comprise using the electrical detector to measure the capacitance between two or more electrodes provided in a section of the one or more tubes or flow lines.

The ultrasonic transmission detector and/or the ultrasonic reflectance detector may comprise one or more ultrasonic transmitter and detector pairs.

The method may comprise using the ultrasonic transmission detector and/or the ultrasonic reflectance detector to detect aspirated liquid by detecting changes in an ultrasonic signal due to aspirated liquid absorbing ultrasonic energy.

The method may comprise absorbing and/or capturing and/or discarding aspirated liquid using one or more porous and/or absorbent materials.

The liquid trap or separator may comprise one or more tubes or flow lines formed at least in part from the one or more porous and/or absorbent materials.

The method may comprise passing the aerosol, smoke or vapour and/or liquid through the one or more tubes or flow lines formed at least in part from the one or more porous and/or absorbent materials.

The liquid trap or separator may comprise a centrifugal liquid separator.

The liquid trap or separator may comprise a sealed chamber comprising an inlet, and the method may comprise introducing the aerosol, smoke or vapour and/or liquid into the chamber though the inlet.

The sealed chamber may comprise an outlet, and the method may comprise allowing the aerosol, smoke or vapour to leave the chamber or extracting the aerosol, smoke or vapour through the outlet without liquid substantially leaving the chamber.

In use an exit of the inlet may be located below an entrance of the outlet.

The method may comprise generating feedback and/or an alarm and/or an alert to a user when the liquid trap or separator contains liquid at or close to a maximum level.

The method may comprise reducing or stopping electrical power to or otherwise disabling the first device in the event that the liquid trap or separator contains liquid at or close to a maximum level.

The liquid may comprise water, saliva, digestive fluids, chyme, saline, blood, urine, mucus and/or one or more other bodily fluids.

According to an aspect there is provided a method of mass spectrometry and/or ion mobility spectrometry comprising the method as described above.

The method may comprise passing the aerosol, smoke and/or vapour into a vacuum chamber of a mass and/or ion mobility spectrometer.

The method may comprise ionising the aerosol, smoke and/or vapour to form analyte ions.

The method may comprise impacting the aerosol, smoke and/or vapour upon a collision surface to form the analyte ions.

The method may comprise heating the collision surface.

The method may comprise heating the collision surface to a temperature selected from the group consisting of: (i) about <100° C.; (ii) about 100-200° C.; (iii) about 200-300° C.; (iv) about 300-400° C.; (v) about 400-500° C.; (vi) about 500-600° C.; (vii) about 600-700° C.; (viii) about 700-800° C.; (ix) about 800-900° C.; (x) about 900-1000° C.; (xi) about 1000-1100° C.; and (xii) about >1100° C.

The method may comprise adding a matrix to the aerosol, smoke and/or vapour.

The method may comprise adding the matrix to the aerosol, smoke and/or vapour prior to the aerosol, smoke and/or vapour impacting upon the collision surface.

The matrix may be selected from the group consisting of: (i) a solvent for the aerosol, smoke and/or vapour; (ii) an organic solvent; (iii) a volatile compound; (iv) polar molecules; (v) water; (vi) one or more alcohols; (vii) methanol; (viii) ethanol; (ix) isopropanol; (x) acetone; and (xi) acetonitrile.

The matrix may comprise a lockmass, lock mobility or calibration compound.

The method may comprise analysing the aerosol, smoke, vapour and/or the analyte ions using the analyser.

Analysing the aerosol, smoke, vapour and/or the analyte ions may comprise: (i) mass analysing and/or ion mobility analysing the aerosol, smoke, vapour, or the analyte ions and/or ions derived from the aerosol, smoke, vapour, the analyte ions; (ii) determining the ion mobility, collision cross section or interaction cross section of the aerosol, smoke, vapour, or the analyte ions and/or ions derived from the aerosol, smoke, vapour, the analyte ions; and/or (iii) fragmenting or reacting the aerosol, smoke, vapour, or the analyte ions.

Various embodiments are contemplated wherein analyte ions generated by the ambient ionisation ion source are then subjected either to: (i) mass analysis by a mass analyser or filter such as a quadrupole mass analyser or a Time of Flight mass analyser; (ii) ion mobility analysis (IMS) and/or differential ion mobility analysis (DMA) and/or Field Asymmetric Ion Mobility Spectrometry (FAIMS) analysis; and/or (iii) a combination of firstly ion mobility analysis (IMS) and/or differential ion mobility analysis (DMA) and/or Field Asymmetric Ion Mobility Spectrometry (FAIMS) analysis followed by secondly mass analysis by a mass analyser or filter such as a quadrupole mass analyser or a Time of Flight mass analyser (or vice versa). Various embodiments also relate to an ion mobility spectrometer and/or mass analyser and a method of ion mobility spectrometry and/or method of mass analysis.

The method may comprise providing real time and/or delayed information to a user of the first device.

The information may comprise mass and/or ion mobility spectral information and/or tissue classification information.

The method may comprise generating feedback and/or an alarm and/or an alert to a user of the first device when tissue or other matter from an undesired target region or area is being analysed.

The method may comprise reducing or stopping electrical power to or otherwise disabling the first device in the event that tissue or other matter from an undesired target region or area is being analysed.

The method may comprise generating feedback and/or an alarm and/or an alert to a user of the first device when the first device is operating in and/or is located in an undesired target region or area.

The method may comprise reducing or stopping electrical power to or otherwise disabling the first device in the event that the electrosurgical tool is operating in and/or is located in an undesired target region or area.

The method may comprise analysing said aerosol, smoke, vapour and/or the analyte ions to produce mass and/or ion mobility spectrometric data and analysing the mass and/or ion mobility spectrometric data.

Analysing the mass and/or ion mobility spectrometric data may comprise analysing one or more sample spectra so as to classify an aerosol, smoke or vapour sample.

Analysing the one or more sample spectra so as to classify the aerosol, smoke or vapour sample may comprise supervised analysis of the one or more sample spectra and/or unsupervised analysis of the one or more sample spectra.

Analysing the one or more sample spectra so as to classify the aerosol, smoke or vapour sample may comprise using one or more of: univariate analysis; multivariate analysis; principal component analysis (PCA); linear discriminant analysis (LDA); maximum margin criteria (MMC); library-based analysis; soft independent modelling of class analogy (SIMCA); factor analysis (FA); recursive partitioning (decision trees); random forests; independent component analysis (ICA); partial least squares discriminant analysis (PLS-DA); orthogonal (partial least squares) projections to latent structures (OPLS); OPLS discriminant analysis (OPLS-DA); support vector machines (SVM); (artificial) neural networks; multilayer perceptron; radial basis function (RBF) networks; Bayesian analysis; cluster analysis; a kernelized method; and subspace discriminant analysis.

Analysing the one or more sample spectra so as to classify the aerosol, smoke or vapour sample may comprise developing a classification model or library using one or more reference sample spectra.

Analysing the one or more sample spectra so as to classify the aerosol, smoke or vapour sample may comprise performing linear discriminant analysis (LDA) after performing principal component analysis (PCA).

Analysing the one or more sample spectra so as to classify the aerosol, smoke or vapour sample may comprise performing a maximum margin criteria (MMC) process after performing principal component analysis (PCA).

Analysing the one or more sample spectra so as to classify the aerosol, smoke or vapour sample may comprise defining one or more classes within a classification model or library.

Analysing the one or more sample spectra so as to classify the aerosol, smoke or vapour sample may comprise defining one or more classes within a classification model or library manually or automatically according to one or more class or cluster criteria.

The one or more class or cluster criteria for each class may be based on one or more of: a distance between one or more pairs of reference points for reference sample spectra within a model space; a variance value between groups of reference points for reference sample spectra within a model space; and a variance value within a group of reference points for reference sample spectra within a model space.

The one or more classes may be each defined by one or more class definitions.

The one or more class definitions may comprise one or more of: a set of one or more reference points for reference sample spectra, values, boundaries, lines, planes, hyperplanes, variances, volumes, Voronoi cells, and/or positions, within a model space; and one or more positions within a class hierarchy.

Analysing the one or more sample spectra so as to classify the aerosol, smoke or vapour sample may comprise using a classification model or library to classify one or more unknown sample spectra.

Analysing the one or more sample spectra so as to classify the aerosol, smoke or vapour sample may comprise classifying one or more sample spectra manually or automatically according to one or more classification criteria.

The one or more classification criteria may comprise one or more of:

a distance between one or more projected sample points for one or more sample spectra within a model space and a set of one or more reference points for one or more reference sample spectra, values, boundaries, lines, planes, hyperplanes, volumes, Voronoi cells, or positions, within the model space being below a distance threshold or being the lowest such distance;

a position for one or more projected sample points for one or more sample spectra within a model space being one side or other of one or more reference points for one or more reference sample spectra, values, boundaries, lines, planes, hyperplanes, or positions, within the model space;

a position for one or more projected sample points for one or more sample spectra within a model space being within one or more volumes or Voronoi cells within the model space; and a probability or classification score being above a probability or classification score threshold or being the highest such probability or classification score.

According to an aspect there is provided a method of electrosurgery comprising:

contacting biological tissue with a first device and activating the first device so as to generate aerosol, smoke and/or vapour;

aspirating aerosol, smoke, vapour and/or liquid and capturing and/or discarding aspirated liquid before causing the remaining aspirated aerosol, smoke and/or vapour to impact upon a collision surface located within a vacuum chamber of a mass and/or ion mobility spectrometer in order to form analyte ions; and analysing the analyte ions.

According to an aspect there is provided electrosurgical apparatus comprising:

a first device comprising arranged and adapted to generate aerosol, smoke or vapour from a target;

a device arranged and adapted to activate the first device when the first device is in contact, in use, with biological tissue so as to generate aerosol, smoke or vapour;

a device arranged and adapted to aspirate aerosol, smoke, vapour and/or liquid;

a device arranged and adapted to capture and/or discard aspirated liquid; and a mass and/or ion mobility spectrometer comprising: (i) a collision surface located within a vacuum chamber of the mass and/or ion mobility spectrometer wherein, in use, remaining aerosol, smoke and/or vapour is arranged to impact upon the collision surface so as to form analyte ions; and (ii) an analyser for analysing the analyte ions.

According to an aspect there is provided a mass and/or ion mobility spectrometer comprising apparatus as described above.

According to an aspect there is provided a method of mass spectrometry and/or ion mobility spectrometry comprising a method as described above.

According to an aspect there is provided apparatus for performing rapid evaporative ionisation mass spectrometry ("REIMS") comprising:

an electrosurgical tool comprising one or more electrodes;

one or more devices arranged and adapted to aspirate analyte, smoke, fumes, liquid, gas, surgical smoke, aerosol or vapour to or towards an analyser for analysis; and a liquid trap or separator arranged and adapted to capture and/or discard liquid aspirated by the one or more devices.

The apparatus may further comprise an endoscope.

The electrosurgical tool may be arranged and adapted to be deployed through a port in the endoscope.

The liquid trap or separator may be arranged and adapted to remain, in use, external from the endoscope.

The one or more devices may comprise one or more tubes or flow lines which are arranged and adapted to connect the electrosurgical tool to the liquid trap or separator and/or to connect the electrosurgical tool to the analyser.

The one or more tubes or flow lines may comprise: (i) one or more first tubes or flow lines arranged and adapted to connect the electrosurgical tool to the liquid trap or separator; and (ii) one or more second tubes or flow lines arranged and adapted to connect the liquid trap or separator to the analyser.

The one or more devices may be arranged and adapted to transport the aspirated analyte, smoke, fumes, liquid, gas, surgical smoke, aerosol and/or vapour to or towards the analyser through the one or more tubes or flow lines.

The one or more devices may comprise one or more pumps which are arranged and adapted to cause the analyte, smoke, fumes, liquid, gas, surgical smoke, aerosol and/or vapour to be transported to or towards the analyser.

The liquid trap or separator may comprise a liquid detector which is arranged and adapted to detect aspirated liquid.

The apparatus may be arranged and adapted such that if the liquid detector detects aspirated liquid then the liquid trap or separator may be further arranged and adapted to capture and/or discard at least some of the liquid.

The liquid trap or separator may further comprise a liquid collector.

The apparatus may be arranged and adapted such that if the liquid detector detects aspirated liquid then the liquid trap or separator may be further arranged and adapted to divert at least some of the liquid to the liquid collector.

The liquid detector may comprise an optical transmission detector and/or an optical reflection detector.

The liquid trap or separator may comprise one or more porous and/or absorbent materials arranged and adapted to absorb and/or capture and/or discard aspirated liquid.

The liquid trap or separator may comprise one or more tubes or flow lines formed at least in part from one or more porous and/or absorbent materials.

The liquid trap or separator may be arranged and adapted to pass the analyte, smoke, fumes, liquid, gas, surgical smoke, aerosol and/or vapour through the one or more tubes or flow lines formed at least in part from the one or more porous and/or absorbent materials.

The liquid trap or separator may comprise a centrifugal liquid separator.

The liquid trap or separator may comprise a sealed chamber comprising an inlet, wherein the liquid trap or separator is arranged and adapted such that in use the analyte, smoke, fumes, liquid, gas, surgical smoke, aerosol and/or vapour are introduced into the chamber though the inlet.

The sealed chamber may further comprise an outlet, wherein the liquid trap or separator is arranged and adapted such that in use analyte, smoke, fumes, gas, surgical smoke, aerosol and/or vapour can leave the chamber through the outlet substantially without liquid leaving the chamber.

An exit of the inlet may be located below an entrance of the outlet.

According to another aspect there is provided a mass and/or ion mobility spectrometer comprising apparatus as described above.

The mass and/or ion mobility spectrometer may further comprise tubing which is arranged and adapted to pass the analyte, smoke, fumes, gas, surgical smoke, aerosol and/or vapour into a vacuum chamber of the mass and/or ion mobility spectrometer.

The mass and/or ion mobility spectrometer may further comprise a collision surface located within a vacuum chamber of the mass and/or ion mobility spectrometer.

The mass and/or ion mobility spectrometer may further comprise a device which is arranged and adapted so as to cause at least some of the analyte, smoke, fumes, gas, surgical smoke, aerosol and/or vapour to impact upon the collision surface.

The collision surface may be arranged and adapted so that at least some of the analyte, smoke, fumes, gas, surgical smoke, aerosol and/or vapour is ionised upon impact with the collision surface in order to form analyte ions.

The mass and/or ion mobility spectrometer may further comprise a mass analyser or filter and/or ion mobility analyser which is arranged and adapted to mass analyse and/or ion mobility analyse the analyte ions.

The mass and/or ion mobility spectrometer may further comprise a heating device which is arranged and adapted to heat the collision surface.

The heating device may be arranged and adapted to heat the collision surface to a temperature selected from the group consisting of: (i) about <100° C.; (ii) about 100-200° C.; (iii) about 200-300° C.; (iv) about 300-400° C.; (v) about 400-500° C.; (vi) about 500-600° C.; (vii) about 600-700° C.; (viii) about 700-800° C.; (ix) about 800-900° C.; (x) about 900-1000° C.; (xi) about 1000-1100° C.; and (xii) about >1100° C.

The mass and/or ion mobility spectrometer may further comprise a device which is arranged and adapted to add a matrix to the analyte, smoke, fumes, liquid, gas, surgical smoke, aerosol and/or vapour.

The matrix may be added, in use, to the analyte, smoke, fumes, liquid, gas, surgical smoke, aerosol and/or vapour prior to the analyte, smoke, fumes, gas, surgical smoke, aerosol and/or vapour impacting upon the collision surface.

The matrix may be selected from the group consisting of: (i) a solvent for the analyte, smoke, fumes, liquid, gas, surgical smoke, aerosol and/or vapour; (ii) an organic solvent; (iii) a volatile compound; (iv) polar molecules; (v) water; (vi) one or more alcohols; (vii) methanol; (viii) ethanol; (ix) isopropanol; (x) acetone; and (xi) acetonitrile.

The matrix may comprise a lockmass, lock mobility or calibration compound.

The mass and/or ion mobility spectrometer may further comprise a device which is arranged and adapted to provide real time and/or delayed information to a user of the electrosurgical tool.

The information may comprise mass and/or ion mobility spectral information and/or tissue classification information.

The mass and/or ion mobility spectrometer may further comprise a device which is arranged and adapted to generate feedback and/or an alarm and/or an alert to a user of the electrosurgical tool that tissue or other matter from an undesired target region or area is being mass analysed and/or ion mobility analysed.

The mass and/or ion mobility spectrometer may further comprise a device which is arranged and adapted to reduce or stop electrical power to the electrosurgical tool in the event that tissue or other matter from an undesired target region or area is being mass analysed and/or ion mobility analysed.

The mass and/or ion mobility spectrometer may further comprise a device which is arranged and adapted to generate feedback and/or an alarm and/or an alert to a user of the electrosurgical tool that the electrosurgical tool is operating in and/or is located in an undesired target region or area.

The mass and/or ion mobility spectrometer may further comprise a device which is arranged and adapted to reduce or stop electrical power to the electrosurgical tool in the event that the electrosurgical tool is operating in and/or is located in an undesired target region or area.

According to an aspect there is provided a method of rapid evaporative ionisation mass spectrometry ("REIMS") comprising:

providing an electrosurgical tool comprising one or more electrodes;

aspirating analyte, smoke, fumes, liquid, gas, surgical smoke, aerosol and/or vapour to or towards an analyser for analysis; and using a liquid trap or separator to capture and/or discard aspirated liquid.

The method may further comprise providing an endoscope.

The method may further comprise deploying the electrosurgical tool through a port in the endoscope.

The liquid trap or separator may be arranged and adapted to remain, in use, external from the endoscope.

The step of aspirating analyte, smoke, fumes, liquid, gas, surgical smoke, aerosol and/or vapour may further comprise aspirating the analyte, smoke, fumes, liquid, gas, surgical smoke, aerosol and/or vapour through one or more tubes or flow lines which connect the electrosurgical tool to the liquid trap or separator and/or which connect the electrosurgical tool to the analyser.

The one or more tubes or flow lines may comprise: (i) one or more first tubes or flow lines arranged and adapted to connect the electrosurgical tool to the liquid trap or separator; and (ii) one or more second tubes or flow lines arranged and adapted to connect the liquid trap or separator to the analyser.

The method may further comprise transporting the aspirated analyte, smoke, fumes, liquid, gas, surgical smoke, aerosol and/or vapour to or towards the analyser through the one or more tubes or flow lines.

The liquid trap or separator may comprise a liquid detector arranged and adapted to detect aspirated liquid.

If the liquid detector detects aspirated liquid then the liquid trap or separator may be further arranged and adapted to capture and/or discard at least some of the liquid.

The liquid trap or separator may further comprise a liquid collector.

If the liquid detector detects aspirated liquid then the liquid trap or separator may divert at least some of the liquid to the liquid collector.

The liquid detector may comprise an optical transmission detector and/or an optical reflection detector.

The liquid trap or separator may comprise one or more porous and/or absorbent materials arranged and adapted to absorb and/or capture and/or discard aspirated liquid.

The liquid trap or separator may comprise one or more tubes or flow lines formed at least in part from the one or more porous and/or absorbent materials.

The liquid trap or separator may be arranged and adapted to pass the analyte, smoke, fumes, liquid, gas, surgical smoke, aerosol and/or vapour through the one or more tubes or flow lines formed at least in part from the one or more porous and/or absorbent materials.

The liquid trap or separator may comprise a centrifugal liquid separator.

The liquid trap or separator may comprise a sealed chamber comprising an inlet, wherein the liquid trap or separator is arranged and adapted such that in use the analyte, smoke, fumes, liquid, gas, surgical smoke, aerosol and/or vapour are introduced into the chamber though the inlet.

The sealed chamber may further comprise an outlet, wherein the liquid trap or separator is arranged and adapted such that in use analyte, smoke, fumes, gas, surgical smoke, aerosol and/or vapour can leave the chamber through the outlet substantially without liquid leaving the chamber.

An exit of the inlet may be located below an entrance of the outlet.

According to another aspect there is provided a method of mass spectrometry and/or ion mobility spectrometry comprising a method as described above.

The method may further comprise passing the analyte, smoke, fumes, gas, surgical smoke, aerosol and/or vapour through tubing into a vacuum chamber of a mass and/or ion mobility spectrometer.

The method may further comprise providing a collision surface located within a vacuum chamber of the mass and/or ion mobility spectrometer.

The method may further comprise causing at least some of the analyte, smoke, fumes, gas, surgical smoke, aerosol and/or vapour to impact upon the collision surface.

The collision surface may be arranged and adapted so that at least some of the analyte, smoke, fumes, gas, surgical smoke, aerosol and/or vapour is ionised upon impact with the collision surface in order to form analyte ions.

The method may further comprise mass analysing and/or ion mobility analysing the analyte ions.

The method may further comprise heating the collision surface.

The method may further comprise heating the collision surface to a temperature selected from the group consisting of: (i) about <100° C.; (ii) about 100-200° C.; (iii) about 200-300° C.; (iv) about 300-400° C.; (v) about 400-500° C.; (vi) about 500-600° C.; (vii) about 600-700° C.; (viii) about 700-800° C.; (ix) about 800-900° C.; (x) about 900-1000° C.; (xi) about 1000-1100° C.; and (xii) about >1100° C.

The method may further comprise adding a matrix to the analyte, smoke, fumes, liquid, gas, surgical smoke, aerosol and/or vapour.

The method may further comprise adding the matrix to the analyte, smoke, fumes, liquid, gas, surgical smoke, aerosol and/or vapour prior to the analyte, smoke, fumes, gas, surgical smoke, aerosol and/or vapour impacting upon the collision surface.

The matrix may be selected from the group consisting of: (i) a solvent for the analyte, smoke, fumes, liquid, gas, surgical smoke, aerosol and/or vapour; (ii) an organic solvent; (iii) a volatile compound; (iv) polar molecules; (v) water; (vi) one or more alcohols; (vii) methanol; (viii) ethanol; (ix) isopropanol; (x) acetone; and (xi) acetonitrile.

The matrix may comprise a lockmass, lock mobility or calibration compound.

The method may further comprise providing real time and/or delayed information to a user of the electrosurgical tool.

The information may comprise mass and/or ion mobility spectral information and/or tissue classification information.

The method may further comprise generating feedback and/or an alarm and/or an alert to a user of the electrosurgical tool that tissue or other matter from an undesired target region or area is being mass analysed and/or ion mobility analysed.

The method may further comprise reducing or stopping electrical power to the electrosurgical tool in the event that tissue or other matter from an undesired target region or area is being mass analysed and/or ion mobility analysed.

The method may further comprise generating feedback and/or an alarm and/or an alert to a user of the electrosurgical tool that the electrosurgical tool is operating in and/or is located in an undesired target region or area.

The method may further comprise reducing or stopping electrical power to the electrosurgical tool in the event that the electrosurgical tool is operating in and/or is located in an undesired target region or area.

According to another aspect there is provided a method of electrosurgery comprising:
contacting biological tissue with an electrosurgical tool and activating the electrosurgical tool so as to generate analyte, smoke, fumes, liquid, gas, surgical smoke, aerosol and/or vapour;
aspirating the analyte, smoke, fumes, liquid, gas, surgical smoke, aerosol and/or vapour and capturing and/or discarding aspirated liquid before causing the remaining aspirated analyte, smoke, fumes, gas, surgical smoke, aerosol and/or vapour to impact upon a collision surface located within a vacuum chamber of a mass and/or ion mobility spectrometer in order to form analyte ions; and
mass analysing and/or ion mobility analysing the analyte ions.

According to another aspect there is provided an Electrosurgical apparatus comprising:
a rapid evaporative ionisation mass spectrometry ("REIMS") electrosurgical tool comprising one or more electrodes;
a device arranged and adapted to activate the electrosurgical tool when the electrosurgical tool is in contact, in use, with biological tissue so as to generate analyte, smoke, fumes, liquid, gas, surgical smoke, aerosol and/or vapour;
a device arranged and adapted to aspirate the analyte, smoke, fumes, liquid, gas, surgical smoke, aerosol and/or vapour;
a device arranged and adapted to capture and/or discard aspirated liquid; and
a mass and/or ion mobility spectrometer comprising: (i) a collision surface located within a vacuum chamber of the mass and/or ion mobility spectrometer wherein, in use, remaining analyte, smoke, fumes, gas, surgical smoke, aerosol and/or vapour is arranged to impact upon the collision surface so as to form analyte ions; and (ii) a mass and/or ion mobility analyser for mass analysing and/or ion mobility analysing the analyte ions.

The mass and/or ion mobility spectrometer may obtain data in negative ion mode only, positive ion mode only, or in both positive and negative ion modes. Positive ion mode spectrometric data may be combined or concatenated with negative ion mode spectrometric data.

Ion mobility spectrometric data may be obtained using different ion mobility drift gases and/or dopants. This data may then be combined or concatenated.

Various embodiments are contemplated which relate to generating smoke, aerosol or vapour from a target (details of which are provided elsewhere herein) using an ambient ionisation ion source. The aerosol, smoke or vapour may then be mixed with a matrix and aspirated into a vacuum chamber of a mass spectrometer and/or ion mobility spectrometer. The mixture may be caused to impact upon a collision surface causing the aerosol, smoke or vapour to be ionised by impact ionization which results in the generation of analyte ions. The resulting analyte ions (or fragment or product ions derived from the analyte ions) may then be mass analysed and/or ion mobility analysed and the resulting mass spectrometric data and/or ion mobility spectrometric data may be subjected to multivariate analysis or other mathematical treatment in order to determine one or more properties of the target in real time.

According to an embodiment the first device for generating aerosol, smoke or vapour from the target may comprise a tool which utilises an RF voltage, such as a continuous RF waveform.

Other embodiments are contemplated wherein the first device for generating aerosol, smoke or vapour from the target may comprise an argon plasma coagulation ("APC") device. An argon plasma coagulation device involves the use of a jet of ionised argon gas (plasma) that is directed through a probe. The probe may be passed through an endoscope. Argon plasma coagulation is essentially a non-contact process as the probe is placed at some distance from the target. Argon gas is emitted from the probe and is then ionized by a high voltage discharge (e.g., 6 kV). High-frequency electric current is then conducted through the jet of gas, resulting in coagulation of the target on the other end of the jet. The depth of coagulation is usually only a few millimetres.

The first device, surgical or electrosurgical tool, device or probe or other sampling device or probe disclosed in any of the aspects or embodiments herein may comprise a non-contact surgical device, such as one or more of a hydrosurgical device, a surgical water jet device, an argon plasma coagulation device, a hybrid argon plasma coagulation device, a water jet device and a laser device.

A non-contact surgical device may be defined as a surgical device arranged and adapted to dissect, fragment, liquefy, aspirate, fulgurate or otherwise disrupt biologic tissue without physically contacting the tissue. Examples include laser devices, hydrosurgical devices, argon plasma coagulation devices and hybrid argon plasma coagulation devices.

As the non-contact device may not make physical contact with the tissue, the procedure may be seen as relatively safe and can be used to treat delicate tissue having low intracellular bonds, such as skin or fat.

According to various embodiments the mass spectrometer and/or ion mobility spectrometer may obtain data in negative ion mode only, positive ion mode only, or in both positive and negative ion modes. Positive ion mode spectrometric data may be combined or concatenated with negative ion mode spectrometric data. Negative ion mode can provide particularly useful spectra for classifying aerosol, smoke or vapour samples, such as aerosol, smoke or vapour samples from targets comprising lipids.

Ion mobility spectrometric data may be obtained using different ion mobility drift gases, or dopants may be added to the drift gas to induce a change in drift time of one or more species. This data may then be combined or concatenated.

It will be apparent that the requirement to add a matrix or a reagent directly to a sample may prevent the ability to perform in vivo analysis of tissue and also, more generally, prevents the ability to provide a rapid simple analysis of target material.

According to other embodiments the ambient ionisation ion source may comprise an ultrasonic ablation ion source or a hybrid electrosurgical—ultrasonic ablation source that generates a liquid sample which is then aspirated as an aerosol. The ultrasonic ablation ion source may comprise a focused or unfocussed ultrasound.

Optionally, the first device comprises or forms part of an ion source selected from the group consisting of: (i) a rapid evaporative ionisation mass spectrometry ("REIMS") ion source; (ii) a desorption electrospray ionisation ("DESI") ion source; (iii) a laser desorption ionisation ("LDI") ion source; (iv) a thermal desorption ion source; (v) a laser diode thermal desorption ("LDTD") ion source; (vi) a desorption electro-flow focusing ("DEFFI") ion source; (vii) a dielectric barrier discharge ("DBD") plasma ion source; (viii) an Atmospheric Solids Analysis Probe ("ASAP") ion source; (ix) an ultrasonic assisted spray ionisation ion source; (x) an easy ambient sonic-spray ionisation ("EASI") ion source; (xi) a desorption atmospheric pressure photoionisation ("DAPPI") ion source; (xii) a paperspray ("PS") ion source; (xiii) a jet desorption ionisation ("JeDI") ion source; (xiv) a touch spray ("TS") ion source; (xv) a nano-DESI ion source; (xvi) a laser ablation electrospray ("LAESI") ion source; (xvii) a direct analysis in real time ("DART") ion source; (xviii) a probe electrospray ionisation ("PESI") ion source; (xix) a solid-probe assisted electrospray ionisation ("SPA-ESI") ion source; (xx) a cavitron ultrasonic surgical aspirator ("CUSA") device; (xxi) a hybrid CUSA-diathermy device; (xxii) a focussed or unfocussed ultrasonic ablation device; (xxiii) a hybrid focussed or unfocussed ultrasonic ablation and diathermy device; (xxiv) a microwave resonance device; (xxv) a pulsed plasma RF dissection device; (xxvi) an argon plasma coagulation device; (xxvi) a hybrid pulsed plasma RF dissection and argon plasma coagulation device; (xxvii) a hybrid pulsed plasma RF dissection and JeDI device; (xxviii) a surgical water/saline jet device; (xxix) a hybrid electrosurgery and argon plasma coagulation device; and (xxx) a hybrid argon plasma coagulation and water/saline jet device.

BRIEF DESCRIPTION OF THE DRAWINGS

Various embodiments will now be described, by way of example only, and with reference to the accompanying drawings in which:

FIG. 1 illustrates a method of rapid evaporative ionisation mass spectrometry ("REIMS") wherein an RF voltage is applied to bipolar forceps resulting in the generation of an aerosol or surgical plume which is captured through an irrigation port of the bipolar forceps and is then transferred to a mass and/or ion mobility spectrometer for ionisation and mass and/or ion mobility analysis;

FIG. 6 schematically shows a centrifugal liquid separator in accordance with an embodiment;

DETAILED DESCRIPTION

Figure 2B:
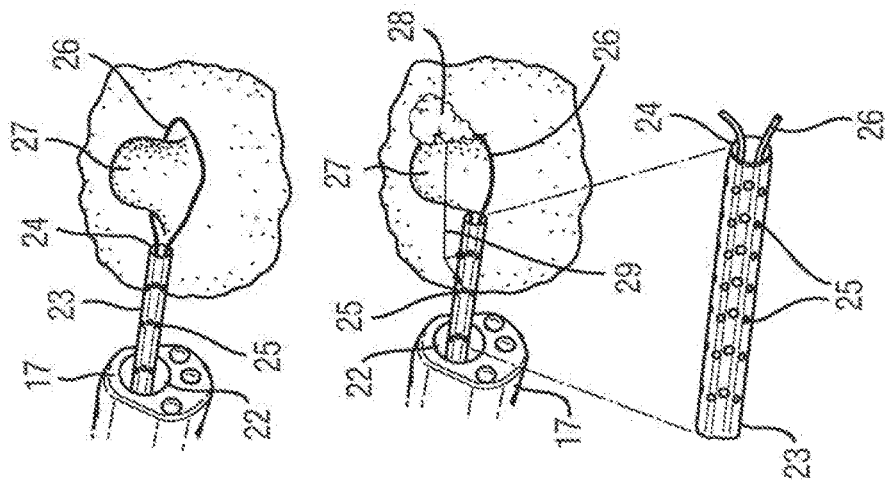
FIG. 2A shows an endoscopic experimental setup according to an embodiment wherein endoscopic tubing is equipped with an additional T-piece in order to establish a direct connection between an electrosurgical electrode tip and a mass and/or ion mobility spectrometer for the transfer of electrosurgical aerosol and FIG. 2B shows resection of a GI polyp according to an embodiment wherein an electrosurgical snare is used to capture a polyp using the snare loop so that the polyp is securely fastened around its base and then electrosurgical dissection is performed and the resulting surgical smoke or aerosol is aspirated through fenestrations provided in the plastic sheath of the electrosurgical tool.

Gastro-intestinal ("GI") cancers account for 23% of cancer-related deaths globally. Despite an increasing incidence, mortality from cancer has been decreasing over the last four decades. However, it is nonetheless estimated that a further 30-40% of these deaths can potentially be prevented. Accurate disease diagnosis and early treatment are key factors in improving cancer outcomes.

Early stage cancers and pre-malignant conditions can be successfully treated using electrocautery-based endoscopic techniques while the gold standard method for diagnosis remains white light endoscopic investigation of the GI tract with tissue biopsy.

It has been recently reported that GI cancer may be missed at endoscopy in up to 7.8% of patients who are subsequently diagnosed with cancer. A major advantage of current endoscopic procedures is that patients avoid the need for major surgery if their lesions are completely excised. However, re-intervention is necessary in up to 41% of patients due to incomplete excision.

As will become further apparent, a particular benefit of a rapid evaporative ionisation mass spectrometry endoscope and snare arrangement according to various embodiments which will be described in more detail below is that the rapid evaporative ionisation mass spectrometry endoscope and snare arrangement enables accurate real time mass and/or ion mobility spectral data to be obtained and utilised in order to reduce mis-diagnosis rates and improve complete resection rates.

Enhanced imaging techniques may also be used to improve diagnostic accuracy within the GI tract with particular emphasis upon spectroscopic characterization using elastic scattering spectroscopy, optical coherence tomography, multimodal imaging combining Raman spectroscopy, autofluorescence and narrow band imaging. However, none of these approaches are currently used in mainstream clinical practice.

Mass spectrometry ("MS") based identification of tissues is known using imaging techniques, sampling probe/electrospray systems and the direct ambient ionisation mass spectrometry investigation of tissues.

Rapid evaporative ionisation mass spectrometry ("REIMS") has emerged from this latter group as a key technology allowing in-situ real-time analysis by the utilization of electrosurgical tools as a mass spectrometry ion source.

The rapid evaporative ionisation mass spectrometry fingerprint of human tissues shows high histological specificity with 90-100% concordance with standard histology.

Various embodiments described herein provide an apparatus for mass spectrometry and/or ion mobility spectrometry which comprises a first device arranged and adapted to generate aerosol, smoke or vapour from a target and one or more second devices arranged and adapted to aspirate aerosol, smoke, vapour and/or liquid to or towards an analyser for analysis. As will be described further below, the apparatus also comprises a liquid trap or separator arranged and adapted to capture and/or discard liquid aspirated by the one or more second devices.

In particular, various embodiments presented herein relate to a real-time, robust tissue characterisation tool which utilises rapid evaporative ionisation mass spectrometry technology.

Various embodiments will now be described in more detail which in general relate to an endoscope coupled with an ambient ionisation ion source. Other non-endoscope based embodiments will also be described.

According to various embodiments, an aerosol, surgical smoke or vapour is generated from a target using the ambient ionisation ion source. The aerosol, surgical smoke or vapour may then be aspirated via one or more aspirations ports or fenestrations into a sheath. The aerosol, surgical smoke or vapour may be passed into a tubing which may transfer the aerosol, surgical smoke or vapour to the inlet of a mass and/or ion mobility spectrometer. The aerosol, surgical smoke or vapour may pass into a vacuum chamber of the mass and/or ion mobility spectrometer and may be caused to impact upon a collision surface causing the aerosol, smoke or vapour to be ionised by impact ionisation which may result in the generation of analyte ions.

The resulting analyte ions (or fragment or product ions derived from the analyte ions) may then be mass analysed and/or ion mobility analysed and the resulting mass and/or ion mobility spectrometric data may then be subjected to multivariate analysis in order to determine one or more properties of the target in real time.

For example, the multivariate analysis may enable a determination to be made as to whether or not a portion of tissue which is currently being resected is cancerous or not.

Ambient Ionisation Ion Sources

According to various embodiments a device is used to generate an aerosol, smoke or vapour from a target (e.g., in vivo tissue). The device may comprise an ambient ionisation ion source which is characterised by the ability to generate analyte aerosol, smoke or vapour from a native or unmodified target. For example, other types of ionisation ion sources such as Matrix Assisted Laser Desorption Ionisation ("MALDI") ion sources require a matrix or reagent to be added to the sample prior to ionisation.

It will be apparent that the requirement to add a matrix or a reagent to a sample prevents the ability to perform in vivo analysis of tissue and also, more generally, prevents the ability to provide a rapid simple analysis of target material.

In contrast, therefore, ambient ionisation techniques are particularly beneficial since firstly they do not require the addition of a matrix or a reagent (and hence are suitable for the analysis of in vivo tissue) and since secondly they enable a rapid simple analysis of target material to be performed.

A number of different ambient ionisation techniques are known and are intended to fall within the scope of the present invention. Desorption Electrospray Ionisation ("DESI") was the first ambient ionisation technique to be developed and was disclosed in 2004. Since 2004, a number of other ambient ionisation techniques have been developed. These ambient ionisation techniques differ in their precise ionisation method but they share the same general capability of generating gas-phase ions directly from native (i.e. untreated or unmodified) samples. A particular benefit of the various ambient ionisation techniques which are intended to fall within the scope of the present invention is that the various ambient ionisation techniques do not require any prior sample preparation. As a result, the various ambient ionisation techniques enable both in vivo tissue and ex vivo tissue samples to be analysed without necessitating the time and expense of adding a matrix or reagent to the tissue sample or other target material.

A list of ambient ionisation techniques which are intended to fall within the scope of the present invention are given in the following table:

| Acronym | Ionisation technique |
|---|---|
| DESI | Desorption electrospray ionisation |
| DeSSI | Desorption sonic spray ionisation |
| DAPPI | Desorption atmospheric pressure photoionisation |
| EASI | Easy ambient sonic-spray ionisation |
| JeDI | Jet desorption electrospray ionisation |
| TM-DESI | Transmission mode desorption electrospray ionisation |
| LMJ-SSP | Liquid microjunction-surface sampling probe |
| DICE | Desorption ionisation by charge exchange |
| Nano-DESI | Nanospray desorption electrospray ionisation |
| EADESI | Electrode-assisted desorption electrospray ionisation |
| APTDCI | Atmospheric pressure thermal desorption chemical ionisation |
| V-EASI | Venturi easy ambient sonic-spray ionisation |
| AFAI | Air flow-assisted ionisation |
| LESA | Liquid extraction surface analysis |
| PTC-ESI | Pipette tip column electrospray ionisation |
| AFADESI | Air flow-assisted desorption electrospray ionisation |
| DEFFI | Desorption electro-flow focusing ionisation |
| ESTASI | Electrostatic spray ionisation |
| PASIT | Plasma-based ambient sampling ionisation transmission |
| DAPCI | Desorption atmospheric pressure chemical ionisation |
| DART | Direct analysis in real time |
| ASAP | Atmospheric pressure solid analysis probe |
| APTDI | Atmospheric pressure thermal desorption ionisation |
| PADI | Plasma assisted desorption ionisation |
| DBDI | Dielectric barrier discharge ionisation |
| FAPA | Flowing atmospheric pressure afterglow |
| HAPGDI | Helium atmospheric pressure glow discharge ionisation |
| APGDDI | Atmospheric pressure glow discharge desorption ionisation |
| LTP | Low temperature plasma |
| LS-APGD | Liquid sampling-atmospheric pressure glow discharge |
| MIPDI | Microwave induced plasma desorption ionisation |

-continued

| Acronym | Ionisation technique |
|---|---|
| MFGDP | Microfabricated glow discharge plasma |
| RoPPI | Robotic plasma probe ionisation |
| PLASI | Plasma spray ionisation |
| MALDESI | Matrix assisted laser desorption electrospray ionisation |
| ELDI | Electrospray laser desorption ionisation |
| LDTD | Laser diode thermal desorption |
| LAESI | Laser ablation electrospray ionisation |
| CALDI | Charge assisted laser desorption ionisation |
| LA-FAPA | Laser ablation flowing atmospheric pressure afterglow |
| LADESI | Laser assisted desorption electrospray ionisation |
| LDESI | Laser desorption electrospray ionisation |
| LEMS | Laser electrospray mass spectrometry |
| LSI | Laser spray ionisation |
| IR-LAMICI | Infrared laser ablation metastable induced chemical ionisation |
| LDSPI | Laser desorption spray post-ionisation |
| PAMLDI | Plasma assisted multiwavelength laser desorption ionisation |
| HALDI | High voltage-assisted laser desorption ionisation |
| PALDI | Plasma assisted laser desorption ionisation |
| ESSI | Extractive electrospray ionisation |
| PESI | Probe electrospray ionisation |
| ND-ESSI | Neutral desorption extractive electrospray ionisation |
| PS | Paper spray |
| DIP-APCI | Direct inlet probe-atmospheric pressure chemical ionisation |
| TS | Touch spray |
| Wooden-tip | Wooden-tip electrospray |
| CBS-SPME | Coated blade spray solid phase microextraction |
| TSI | Tissue spray ionisation |
| RADIO | Radiofrequency acoustic desorption ionisation |
| LIAD-ESI | Laser induced acoustic desorption electrospray ionisation |
| SAWN | Surface acoustic wave nebulization |
| UASI | Ultrasonication-assisted spray ionisation |
| SPA-nanoESI | Solid probe assisted nanoelectrospray ionisation |
| PAUSI | Paper assisted ultrasonic spray ionisation |
| DPESI | Direct probe electrospray ionisation |
| ESA-Py | Electrospray assisted pyrolysis ionisation |
| APPIS | Ambient pressure pyroelectric ion source |
| RASTIR | Remote analyte sampling transport and ionisation relay |
| SACI | Surface activated chemical ionisation |
| DEMI | Desorption electrospray metastable-induced ionisation |
| REIMS | Rapid evaporative ionisation mass spectrometry |
| SPAM | Single particle aerosol mass spectrometry |
| TDAMS | Thermal desorption-based ambient mass spectrometry |
| MAII | Matrix assisted inlet ionisation |
| SAII | Solvent assisted inlet ionisation |
| SwiFERR | Switched ferroelectric plasma ioniser |
| LPTD | Leidenfrost phenomenon assisted thermal desorption |

According to an embodiment the ambient ionisation ion source may comprise a rapid evaporative ionisation mass spectrometry ("REIMS") ion source wherein an RF voltage is applied to one or more electrodes in order to generate an aerosol or plume of surgical smoke by Joule heating.

However, it will be appreciated that other ambient ion sources including those referred to above may also be utilised. For example, according to another embodiment the ambient ionisation ion source may comprise a laser ionisation ion source. According to an embodiment the laser ionisation ion source may comprise a mid-IR laser ablation ion source. For example, there are several lasers which emit radiation close to or at 2.94 μm which corresponds with the peak in the water absorption spectrum. According to various embodiments the ambient ionisation ion source may comprise a laser ablation ion source having a wavelength close to 2.94 μm on the basis of the high absorption coefficient of water at 2.94 μm. According to an embodiment the laser ablation ion source may comprise a Er:YAG laser which emits radiation at 2.94 μm.

Other embodiments are contemplated wherein a mid-infrared optical parametric oscillator ("OPO") may be used to produce a laser ablation ion source having a longer wavelength than 2.94 μm. For example, an Er:YAG pumped ZGP-OPO may be used to produce laser radiation having a wavelength of e.g. 6.1 μm, 6.45 μm or 6.73 μm. In some situations it may be advantageous to use a laser ablation ion source having a shorter or longer wavelength than 2.94 μm since only the surface layers will be ablated and less thermal damage may result. According to an embodiment a Co:MgF2 laser may be used as a laser ablation ion source wherein the laser may be tuned from 1.75-2.5 μm. According to another embodiment an optical parametric oscillator ("OPO") system pumped by a Nd:YAG laser may be used to produce a laser ablation ion source having a wavelength between 2.9-3.1 μm. According to another embodiment a $CO_2$ laser having a wavelength of 10.6 μm may be used to generate the aerosol, smoke or vapour.

According to other embodiments the ambient ionisation ion source may comprise an ultrasonic ablation ion source which generates a liquid sample which is then aspirated as an aerosol. The ultrasonic ablation ion source may comprise a focused or unfocussed source.

According to an embodiment the first device for generating aerosol, smoke or vapour from a target may comprise an electrosurgical tool which may utilise a continuous RF waveform. According to other embodiments a radiofrequency tissue dissection system may be used which is arranged to supply pulsed plasma RF energy to a tool. The tool may comprise, for example, a PlasmaBlade®. Pulsed plasma RF tools operate at lower temperatures than conventional electrosurgical tools (e.g. 40-170° C. c.f. 200-350° C.) thereby reducing thermal injury depth. Pulsed waveforms and duty cycles may be used for both cut and coagulation modes of operation by inducing electrical plasma along the cutting edge(s) of a thin insulated electrode.

Rapid Evaporative Ionisation Mass Spectrometry ("REIMS")

FIG. 1 illustrates a method of rapid evaporative ionisation mass spectrometry ("REIMS") according to an embodiment wherein bipolar forceps 1 may be brought into contact with in vivo tissue 2 of a patient 3. In the embodiment shown in FIG. 1, the bipolar forceps 1 may be brought into contact with brain tissue 2 of a patient 3 during the course of a surgical operation on the patient's brain. An RF voltage from an RF voltage generator 4 may be applied to the bipolar forceps 1 which causes localised Joule or diathermy heating of the tissue 2. As a result, an aerosol or surgical plume 5 is generated. The aerosol or surgical plume 5 may then be captured or otherwise aspirated through an irrigation port of the bipolar forceps 1. The irrigation port of the bipolar forceps 1 is therefore reutilised as an aspiration port. The aerosol or surgical plume 5 may then be passed from the irrigation (aspiration) port of the bipolar forceps 1 to tubing 6 (e.g. ⅛" or 3.2 mm diameter Teflon® tubing). The tubing 6 is arranged to transfer the aerosol or surgical plume 5 to an atmospheric pressure interface 7 of a mass and/or ion mobility spectrometer 8.

As will be described further below, a liquid trap or separator (not shown in FIG. 1) is provided to capture and/or discard any liquid (such as blood) that is captured or otherwise aspirated through the irrigation port of the bipolar forceps 1. Surgical smoke or aerosol which is aspirated via the bipolar forceps 1 is passed to the mass and/or ion mobility spectrometer 8 via the liquid separator or liquid trap in order to remove or reduce the amount of liquid which is onwardly transmitted to the mass and/or ion mobility spectrometer 8.

According to various embodiments a matrix comprising an organic solvent such as isopropanol may be added to the aerosol or surgical plume 5 at the atmospheric pressure interface 7. The mixture of aerosol 3 and organic solvent may then be arranged to impact upon a collision surface within a vacuum chamber of the mass and/or ion mobility spectrometer 8. According to an embodiment the collision surface may be heated. The aerosol is caused to ionise upon impacting the collision surface resulting in the generation of analyte ions. The ionisation efficiency of generating the analyte ions may be improved by the addition of the organic solvent. However, the addition of an organic solvent is not essential.

Analyte ions which are generated by causing the aerosol, smoke or vapour 5 to impact upon the collision surface are then passed through subsequent stages of the mass and/or ion mobility spectrometer and are subjected to mass and/or ion mobility analysis in a mass and/or ion mobility analyser. The mass analyser may, for example, comprise a quadrupole mass analyser or a Time of Flight mass analyser.

Figure 2A:
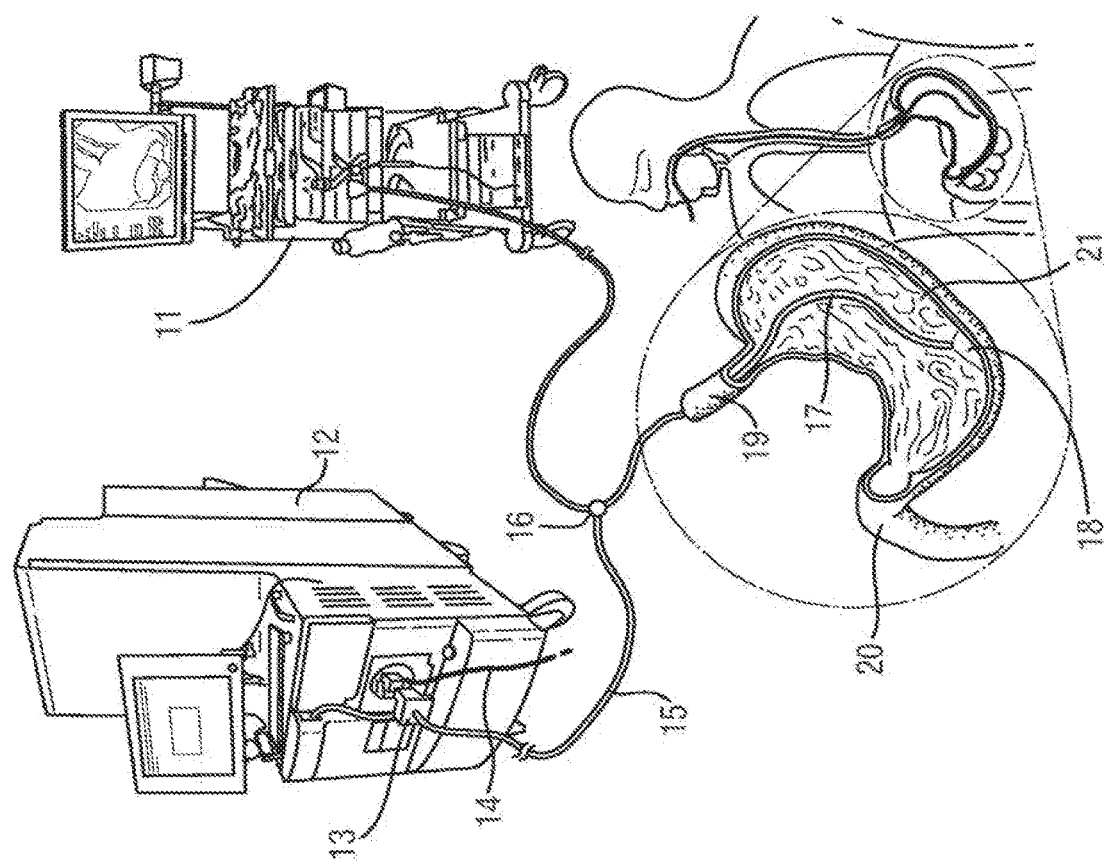

FIGS. 2A and 2B show a rapid evaporative ionisation mass spectrometry ("REIMS") endoscope and snare arrangement in accordance with an embodiment.

According to this embodiment a polypectomy snare 26 is provided. As shown in FIG. 2B, the snare 26 comprises a wire loop which runs through a length of tubing 23. The wire loop is attached to a manipulator which, as shown in FIG. 2A, may be operated by a user via an endoscopic stack 11. The manipulator allows a user to close the snare 26 around a polyp 27. The wire snare 26 is connected to an RF voltage generator (not shown in FIG. 2A). The wire snare 26 acts as an electrosurgical tool and may be deployed through a port 22 in an endoscope 17 and used to resect polyps 27 located e.g., in the stomach 21, pylorus 20, or colon etc., e.g., via the oesophagus 19. As the polypectomy snare 26 is deployed and tightened around a polyp 27, the polyp 27 effectively restricts or seals the open end 24 of the tubing 23 which houses the wire snare 26.

When an RF voltage is applied to the wire snare 26, the wire snare 26 acts as an electrosurgical tool and effectively cuts and removes the polyp 27. At the same time, surgical smoke or aerosol 28 is generated which is substantially unable to pass into the end 24 of the tubing 23 which houses the wire snare 26. The tubing 23 which houses the wire snare 26 may additionally be provided with fenestrations or one or more aspiration ports 25 which enables the surgical smoke or aerosol 28 to be aspirated into the tubing 23 which houses the wire snare 26. The surgical smoke or aerosol 28 may be sucked towards the tubing, e.g. by a pump (not shown in FIG. 2A) connected to the tubing, where the direction of smoke suction may be as illustrated by arrow 29, i.e., the surgical smoke or aerosol 28 may be sucked towards the tubing 23 and through the fenestrations or one or more aspiration ports 25. The surgical smoke or aerosol 28 may be aspirated into and transported along the length of the tubing 23 and, as shown in FIG. 2A, via a connector 16 may be passed to a vacuum chamber of a mass and/or ion mobility spectrometer 12 whereupon the surgical smoke or aerosol may be ionised upon impacting a collision surface which may be heated.

The resulting analyte ions may then be mass analysed and/or ion mobility analysed and real time information relating to the tissue which is being resected is provided to a user (who may be, for example, a surgeon or a specialist nurse). In addition to cutting the polyp 27 away from the lining of the stomach 21 or colon, the snare 26 may also be used to hold on to the polyp 27 so that the polyp 27 can be removed from the stomach 21 or colon, optionally analysed and then disposed of.

The endoscope may emit light 18 and comprise a camera such that a user may appropriately operate the electrosurgical tool and endoscope.

According to various embodiments, a liquid trap or separator (not shown in FIG. 2A) is provided to capture and/or discard any aspirated liquid. Surgical smoke or aerosol which is aspirated via the electrosurgical tool is passed to the mass and/or ion mobility spectrometer 12 via the liquid separator or liquid trap in order to remove or reduce the amount of liquid which is onwardly transmitted to the mass and/or ion mobility spectrometer 12.

According to various other embodiments, the electrosurgical tool and associated endoscope may be used in other body cavities and organs including the lung, nose and urethra. It will accordingly be appreciated that the terms "endoscope", "endoscopic" an "endoscopy", etc., as used herein are intended to encompass arrangements such as bronchoscopes/bronchoscopy, rhinoscopes/rhinoscopy, nasoscopes/nasoscopy, cytoscopes/cystoscopy, and the like.

Where the endoscope is used in the lung, for example, a small amount of lung tissue may be analysed using the electrosurgical tool, e.g. to test for cancer. This could be performed additionally to or instead of obtaining and analysing a biopsy sample. According to an embodiment the snare may comprise a monopolar electrode device and a relatively large pad acting as a return electrode may be placed underneath the patient so that electrical current flows from the snare electrode, through the patient, to the return electrode. Other embodiments are also contemplated wherein the snare electrode may comprise a bipolar device such that electrical current does not flow through the patient's body. A bipolar electrode device may be used, for example, in very sensitive operations such as brain surgery wherein it is clearly undesirable for an electrical current to flow through surrounding tissue.

Although a monopolar or a bipolar electrode arrangement is particularly beneficial, other embodiments are also contemplated wherein the electrosurgical tool may comprise a multi-phase or 3-phase device and may comprise, for example, three or more separate electrodes or probes.

According to another embodiment an optical fibre coupled to a laser source may be used to generate the aerosol, smoke or vapour.

A matrix may be added or mixed with the analyte, smoke, fumes, liquid, gas, surgical smoke, aerosol and/or vapour prior to the analyte, smoke, fumes, liquid, gas, surgical smoke, aerosol and/or vapour impacting upon the collision surface.

The matrix may comprise a solvent for the analyte, smoke, fumes, liquid, gas, surgical smoke, aerosol and/or vapour and/or may comprise an organic solvent and/or a volatile compound.

According to an embodiment the matrix may comprise polar molecules, water, one or more alcohols, methanol, ethanol, isopropanol, acetone or acetonitrile. Isopropanol is particularly beneficial to use.

The matrix which is added may additionally or alternatively comprise a lockmass, lock mobility or calibration compound.

The addition of a matrix is particularly beneficial in that dissolving analyte in the matrix eliminates intermolecular bonding between the analyte molecules. As such, when the dissolved analyte is collided with the collision surface, the dissolved analyte will fragment into droplets and any given droplet is likely to contain fewer analyte molecules than it would if the matrix were not present. This in turn leads to a more efficient generation of ions when the matrix in each droplet is evaporated.

FIG. 2A also shows in more detail how according to an embodiment an endoscopic polypectomy snare may be equipped with an additional T-piece connector 16 in order to establish a transfer line between the tissue evaporation point and the atmospheric inlet 13 of a mass and/or ion mobility spectrometer 12. The atmospheric inlet 13 may comprise a grounding 14.

The rapid evaporative ionisation mass spectrometry ("REIMS") endoscopic setup was initially optimized and its reproducibility was assessed using a porcine stomach model. Artificial polyps were created within porcine stomach mucosa and resections were undertaken using a polypectomy snare 26 as shown in FIG. 2B. This set-up allowed for an exact simulation of a standard endoscopic resection. Since the polyp 27 completely blocks the opening or tool deployment opening 24 of the plastic sheath tubing 23 of the snare 26 during resection as can be seen from FIG. 2B, the aerosol 28 produced by the resection may be aspirated through fenestrations 25 which may be provided on the plastic sheath 23 of the snare 26.

The provision of fenestrations 25 on the plastic sheath 23 of the rapid evaporative ionisation mass spectrometry ("REIMS") snare which are distal from the tool deployment opening 24 of the snare are particularly beneficial since the fenestrations or aspiration ports 25 allow surgical smoke or aerosol 28 to be aspirated when the tool deployment opening 24 is at least partially or totally blocked.

The aerosol particles 28 which enter the tubing 23 housing the rapid evaporative ionisation mass spectrometry ("REIMS") snare 26 via the fenestrations or aspiration ports 25 may then be transferred to a mass and/or ion mobility spectrometer 12 via PTFE tubing 15 which is connected to a port of the snare. The snare 26 may be connected to the proximal end of a rapid evaporative ionisation mass spectrometry ("REIMS") endoscope 17. The tubing 15 may be connected directly to an inlet capillary or ion sampling orifice of the mass and/or ion mobility spectrometer 12. It will be understood that the mass and/or ion mobility spectrometer is distal to the point of evaporation.

Aspiration of the aerosols may be facilitated using a Venturi pump driven by standard medical air or nitrogen.

The mass and/or ion mobility spectrometer may include a modified atmospheric interface which may include a collision surface which is positioned along and adjacent to the central axis of the large opening of a StepWave® ion guide. As will be understood by those skilled in the art, a StepWave® ion guide comprises two conjoined ion tunnel ion guides. Each ion guide comprises a plurality of ring or other electrodes wherein ions pass through the central aperture provided by the ring or other electrodes. Transient DC voltages or potentials are applied to the electrodes. The StepWave® ion guide is based on stacked ring ion guide technology and is designed to maximise ion transmission from the source to the mass and/or ion mobility analyser. The device allows for the active removal of neutral contaminants thereby providing an enhancement to overall signal to noise. The design enables the efficient capture of the diffuse ion cloud entering a first lower stage which is then focused into an upper ion guide for transfer to the mass and/or ion mobility analyser.

The collision surface located within a vacuum chamber of the mass and/or ion mobility spectrometer facilitates efficient fragmentation of molecular clusters formed in the free jet region of the atmospheric interface due to the adiabatic expansion of gas entering the vacuum chamber and the resulting drop of temperature. Other means for facilitating efficient fragmentation of molecular clusters may additionally or alternatively be provided within the vacuum chamber, for example, a collision gas may be provided in this region wherein collisions with the collision gas may help to break up the molecular clusters.

The surface-induced dissociation of supramolecular clusters may improve the signal intensity and also alleviates the problems associated with the contamination of ion optics.

Rapid evaporative ionisation mass spectrometry spectra recorded from the porcine stomach model in the m/z range 600-1000 feature predominantly phospholipids which have been observed for all mammalian tissue types in previous rapid evaporative ionisation mass spectrometry experiments.

Various experiments have been performed in order to optimise the snare tip geometry and also to optimise the number and relative positions of the fenestrations on the plastic sheath of the snare. An assessment of the repeatability of the analysis has also been performed.

Following optimization of the sampling geometry, the rapid evaporative ionisation mass spectrometry endoscopic setup was tested on ex vivo human samples including gastric adenocarcinoma, healthy gastric mucosa and healthy gastric submucosa. The samples were acquired from three individual patients, all of whom provided written informed consent.

According to various embodiments of performing rapid evaporative ionisation mass spectrometry ("REIMS"), an electrosurgical probe comprising an electrosurgical tool and one or more aspiration ports may be provided deployed within an endoscope.

Real time and/or delayed information may be provided to a user of the electrosurgical tool that may comprise mass and/or ion mobility spectral information and/or tissue classification information. A feedback device and/or an alarm and/or an alert may also be provided to provide a user of the electrosurgical tool with feedback and/or an alarm and/or an alert that analyte from an undesired target region or area is being analysed by the analyser or that the electrosurgical tool is operating in and/or is located in an undesired target region or area.

Electrical power to the electrosurgical tool may be reduced and/or stopped in the event that analyte from an undesired target region or area is being analysed by the analyser and/or the electrosurgical tool is operating in and/or is located in an undesired target region or area.

The rapid evaporative ionisation mass spectrometry-based endoscopic setup according to various embodiments addresses various potential problems.

In particular, various embodiments address the problems of the presence of liquids and moisture in the relatively closed endoscopic environment (i.e., in the stomach or intestines, etc.) which necessitates strategies to prevent liquid from reaching the analyser (or at least to reduce the amount of liquid reaching the analyser) since the liquid will not typically be related to the tissue sample of interest and may damage the analyser.

It has been found that strategies designed to reduce the amount of liquid that is initially aspirated into the probe can have disadvantageous side effects on the operation of the device and can often be ineffective because of the relatively closed endoscopic environment.

Accordingly, the method of rapid evaporative ionisation mass spectrometry ("REIMS") analysis according to various embodiments allows for the initial aspiration of undesired liquid by the electrosurgical probe but then removes the undesired liquid before the liquid is able to reach the analyser, i.e. using a liquid trap or separator.

The various embodiments also address the problems associated with restrictions on the size of the electrosurgical probe due to its use in endoscopic environments, as well as potential problems associated with dead volumes, memory effects, trapping of the volume of liquid aspirated during a surgical intervention, cleanability and/or disposability, and potential modification of the composition of the aerosol or surgical smoke by the apparatus.

Although particularly beneficial in the context of performing analysis of endoscopic environments, the apparatus according to various embodiments may also be useful in other situations. Thus, the apparatus need not comprise an endoscope. For example, there a number of applications of the apparatus according to various embodiments in which liquid that is unrelated to a target of interest (that is being analysed by the first device) may be aspirated to or towards the analyser. For example, in various embodiments, saline, blood, urine, mucus and/or other bodily fluids may be aspirated to or towards the analyser when analysing a target (e.g. tissue) of interest. Thus, according to various embodiments, the liquid trap or separator may capture and/or discard any one or more or all of these liquids in order to prevent the liquid reaching (and potentially damaging) the analyser.

Figure 3:
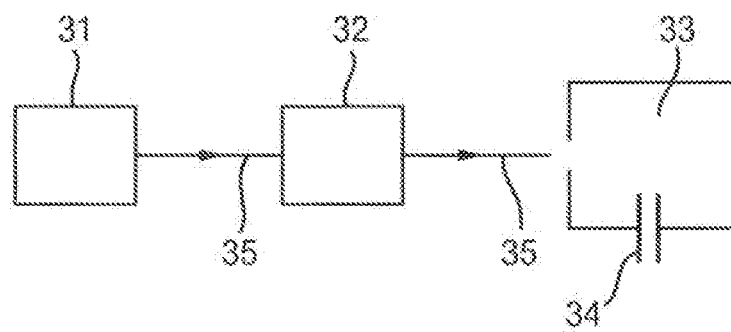
FIG. 3 shows schematically an apparatus according to various embodiments.

In accordance with various embodiments, as shown in FIG. 3, a liquid trap or separator 32 may be provided between an electrosurgical tool or probe 31 and an analyser 33, where the liquid trap or separator 32 captures or discards undesired liquids that are aspirated by the tool or probe 31 whilst allowing the aerosol or surgical smoke itself to pass relatively uninhibited to the analyser 33, e.g. of a mass and/or ion mobility spectrometer. The aerosol, surgical smoke and/or liquid may be aspirated to or towards the analyser 33 for analysis, e.g. by a pump 34 and tubing 35. This setup prevents undesired liquid from reaching the analyser 33 without affecting the measurement of the aerosol or surgical smoke.

The liquid trap or separator 32 may be arranged to capture the liquid, e.g. using a liquid collector, for later disposal.

Feedback and/or an alarm and/or an alert may be provided to a user, e.g. when the liquid trap 32 is or is close to being full. Additionally or alternatively, the apparatus (e.g. the electrosurgical tool 31) may be disabled or partially disabled, e.g. by reducing or stopping electrical power to the apparatus (e.g. to the electrosurgical tool 31) in the event that the liquid trap 32 is or is close to being full. The liquid trap 32 may be provided with one or more liquid detectors for this purpose.

PTFE tubing 35 may be provided to connect the electrosurgical tool 31 to the liquid trap or separator 32, and the liquid trap or separator 32 to the inlet capillary or ion sampling orifice of the mass and/or ion mobility spectrometer. The aspirated surgical smoke or aerosol may be transported to the mass and/or ion mobility spectrometer through the tubing 35.

According to various endoscopic embodiments, when the electrosurgical tool 31 is inserted into the endoscopic environment, the liquid trap or separator 32 may remain external to the endoscopic environment. This avoids the need to provide an additional device for preventing liquid from being aspirated by the electrosurgical tool 31 so that the size of the electrosurgical tool 31 can be kept to a minimum.

The liquid trap or separator 32 may take various different forms.

The features of the liquid trap or separator 32 may include: (i) minimal dead volume in order to ensure fast operation and minimal delay time; (ii) minimal memory effects (which occur when the sample analysed by the mass and/or ion mobility spectrometer does not relate to the sample currently being evaporated by the electrosurgical tool)—in particular the internal geometrical profile of the flow channel of the liquid trap or separator may not cause significant memory effects; (iii) the liquid trap or separator 32 may have a sufficient trapping volume in order to store the liquid aspirated during a surgical intervention; (iv) contaminated surfaces and parts of the liquid trap or separator 32 (i.e., those that come into contact with the liquid) may be easily cleanable or disposable; (v) the material of the parts of the liquid trap or separator 32 that come into contact with the aerosol may not modify the composition of the aerosol so as not to influence the measurement results; and (vi) the liquid trap or separator may be sterile or sterilised.

More specifically, it was determined that the liquid trap or separator 32 according to various embodiments may beneficially meet the following technical parameters: (i) the maximum allowed delay time may be around 2 s with about 750 ml/min gas flow rate (to be added to the inherent delay time of the tube connecting the endoscope and the mass and/or ion mobility spectrometer, which is typically, e.g., about 3 meters in length and about 1.5 mm in internal diameter); (ii) the maximum memory effect may give around 3 s until the signal intensity drops to 10% from the peak maximum; and (iii) the minimum volume of liquid collector may be around 30 ml.

Various embodiments of the liquid trap or separator were tested using the following experimental work flows.

Various liquid traps or separators having a liquid collection vial with a known tare weight were attached to the outlet of an electrosurgical tool or probe. A vacuum pump was connected to the other outlet of the liquid trap or separator to suck air though the system. The flow rate was set to about 750 ml/min.

According to a discontinuous test, about 20 ml of water was aspirated through the inlet by immersing the electrosurgical tool in liquid for about 1 s time periods with a 15 s break between each immersion. This activity was continued until the 20 ml of water had been aspirated. After aspiration of the whole 20 ml, the liquid collection vial was weighed to determine the amount of separated and non-separated liquid.

According to a continuous test, the above measurement was repeated by continuously aspirating 20 ml of water.

Using these measurement methods the liquid separation efficiency and the performance of each liquid trap or separator was determined.

According to tests using a mass spectrometer, a mass spectrometer was attached to the outlet of the electrosurgical tool. Surgical fumes or aerosol was aspirated via the electrosurgical tool. The time between the actual aspiration and the appearance of a mass spectral signal was measured. The measurement was repeated after suction of liquid for about 1 s. The entire operation was repeated three times and the spectrum intensity readings were registered. As a control measurement, the same activity was performed without a liquid trap or separator using a PTFE tube of about 1.5 m length, and about 0.5 mm in internal diameter.

Using these measurements, the delay time, the memory effect and decrease of signal intensity was established.

According to an embodiment the liquid trap or separator may comprise a valve based liquid separator. The aspirated sample may be transferred through a tube detector section where the presence of any unwanted liquid may be detected. If liquid is detected then the sample flow may be diverted to a liquid collector by controlled valves.

Figure 4:
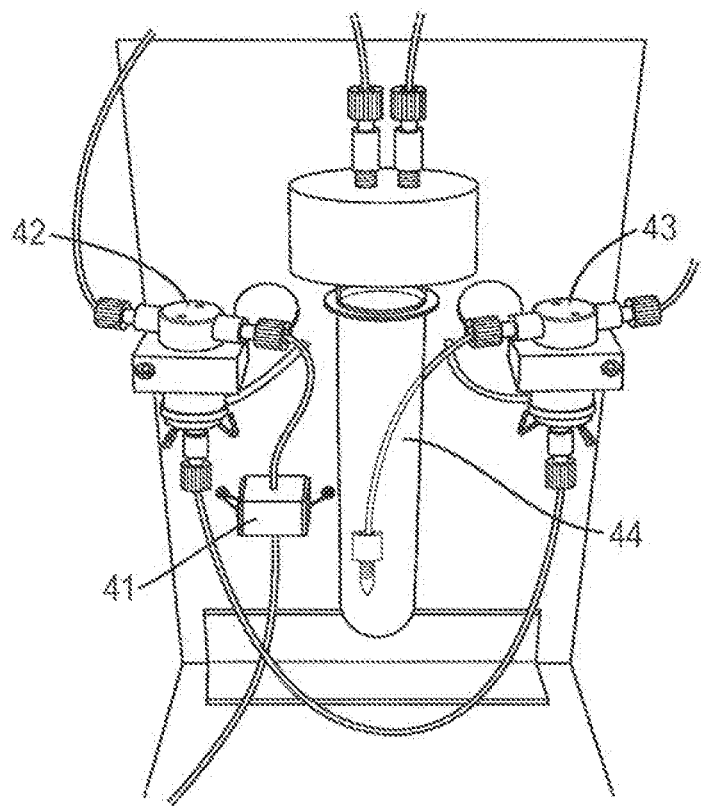
FIG. 4 shows a valve-based liquid separator in accordance with an embodiment.

As shown in FIG. 4, the aspirated sample may be transferred through a detector such as a transmission optical detector 41. Should liquid be present, the transmission increases and as that is detected, a connected electronic controller may send a signal to an inlet selector valve 42, which diverts the sample flow to a liquid collector 44. As a result, the liquid is collected in the liquid collector 44.

Simultaneously, an outlet selector valve 43 may also be commanded such that the air flow coming from the liquid collector 44 is sucked rather than the liquid flow coming from the inlet valve 42. This prevents blocking of the system.

In the event that gas is detected by the detector 41, the electronic controller may reset both valves, so that the aerosol part of the sample flows into the mass and/or ion mobility spectrometer through the inlet and outlet valves.

The liquid detector 41 may be located relatively close to the analyser 33 (e.g. mass and/or ion mobility spectrometer) or more beneficially relatively close to (e.g. as close as possible to) the electrosurgical tool 31 (endoscopic device). This provides more time for the diverter to operate.

Other types of detector may be used to detect liquid, such as for example, an optical transmission detector, an optical reflection detector, an ultrasonic transmission detector, an ultrasonic reflectance detector, and/or an electrical detector.

An electrical detector may comprise, e.g. two or more probes or electrodes for measuring a resistance, voltage, capacitance or current. The probes or electrodes may be embedded into a small section of the sampling tubing, and may be arranged to measure the electrical conductivity, resistance and/or capacitance of the section of the sampling tubing. In this case, when liquid is present, the resistance, voltage or current between the two or more probes will change, allowing the presence of the liquid to be detected.

An ultrasonic detector may comprise an ultrasonic transmitter and detector pair, e.g. embedded in a small section of the sampling tubing. As liquid passes through the tubing the ultrasonic signal received from the ultrasonic transmitter by the ultrasonic detector will change as the liquid absorbs the ultrasonic energy, thereby allowing the presence of liquid to be detected.

A prototype unit was built on an aluminium/PE sandwich panel. PTFE tubes ($1/16$" outer diameter and 1 mm inner diameter) were equipped with standard fittings. Both the inlet and outlet valves were made from PTFE with seats of about 0.5 mm. The detector on the inlet was an opto-gate comprising an LED (having an opening of about 0.5 mm) and a phototransistor.

The device was demonstrated to work as planned. A vent valve may be provided in order to address the fact that during the period of liquid separation, the mass and/or ion mobility spectrometer attached to the outlet sucks gas from above stagnating and already separated liquid.

Exceedingly short delay times (about 0.2 s) were achieved due to the small transfer volume in the aerosol suction phase.

Figure 5A:
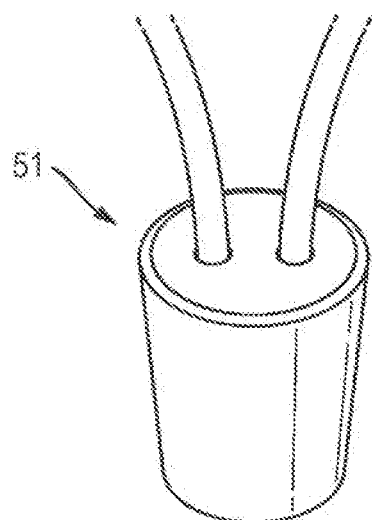
FIG. 5A shows an (incomplete) absorption liquid separator with a silicon rubber tube and FIG. 5B shows a (complete) absorption liquid separator with fittings and PTFE tubing in accordance with an embodiment.
Figure 5B:
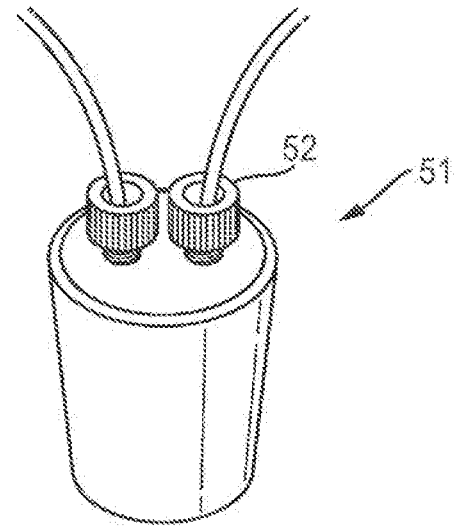
Figure 7:
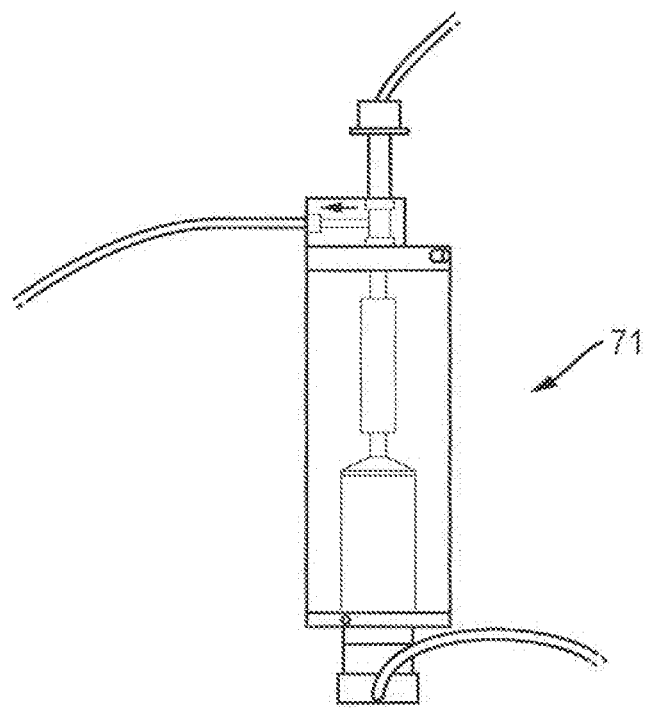
FIG. 7 shows a centrifugal liquid separator in accordance with an embodiment.
Figure 8:
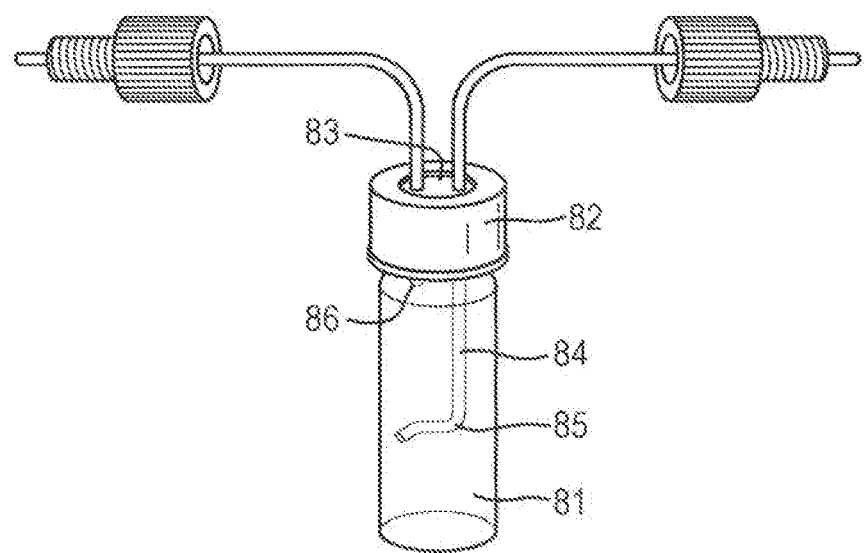
FIG. 8 shows a liquid trap in accordance with an embodiment.

As shown in FIG. 5A and FIG. 5B, according to another embodiment the liquid trap or separator may comprise an absorption based liquid separator 51. The aspirated liquid may be absorbed in a porous, absorbent material (not shown in FIG. 5A and FIG. 5B) in order to prevent the liquid from reaching the outlet of the liquid separator.

The aspirated liquid may be transferred through a tube system made of a moisture absorbent, hydrophilic, capillary structured material. The tube may have a constant bend which causes permanent contact between the liquid and the inner walls of the tubes. The porous material may absorb the liquid content of the sample, so that only the gas will pass through to the outlet.

Gypsum was selected as being the most suitable absorbent material. Gypsum is beneficial due to its absorbency, as well as due to the fact that it can be easily shaped to the desired geometry. A coil or helix shaped silicon rubber tube was cast into gypsum. The tube was removed from the cast once the gypsum hardened. Fittings 52 were attached to the inlet and outlet of the tube, to function as the connection ports of the system.

The device was demonstrated to work as planned. This embodiment beneficially represents a cost-efficient construction thereby allowing disposability. A large volume of tubing may be provided to absorb the required amount of liquid and to address the problem of the absorbency decreasing as the gypsum is saturated with liquid (most probably due to the early saturation of the upper absorbent layer and the hindered migration of liquid towards the inner absorbent layers).

According to another embodiment the liquid trap or separator may comprise a continuously operating centrifugal liquid separator. The liquid separator according to this embodiment is based on the continuous centrifugal separation technique. The design maintains system dead volume as low as possible. A small transfer volume in relation to the required gas flow may be used while maintaining the sufficient capacity of the liquid collector.

As shown in FIG. 6, the centrifugal liquid separator may comprise a double wall coaxial dispenser head 61, a revolving separation cylinder 62, an electric motor with a shaft connector 63 and a liquid collector 64. The sample flow is transferred to the middle of the revolving separation cylinder through the inner tube of the coaxial dispenser. Due to the centrifugal force, the separated liquid slowly migrates up the conical wall of the cylinder. As soon as the liquid reaches the uppermost brim of the cylinder, it flies over to the inner wall of the liquid collector. From there the liquid flows down and gathers at the bottom of the collector. The gas content of the sample forms a thin layer over the climbing droplets and flows to the uppermost part of the separation cylinder from where the gas leaves towards the mass and/or ion mobility spectrometer. The inlet and outlet of the unit 65,66 may be connected by PTFE tubes. In this way, a low transfer volume of the gas flow is ensured.

As shown in FIG. 7 a separator 71 was built and tested. The following parameters were measured for the device and demonstrate the device's excellent operation, namely a delay time of about 1.5-2 s, a memory effect of about 2.5 s and the ability to collect about 35 ml of liquid (this may be increased by geometric shaping). No measurable amount of liquid was transferred into the outlet tank. The mass spectrum of the aerosol passing through the device was not modified. The signal intensity of the spectrum decreased by around 40%.

According to a yet further embodiment the liquid trap or separator may comprise a liquid trap. The liquid trap may comprise a sealed chamber having an inlet though which the surgical smoke or aerosol and the liquid are introduced into the chamber and an outlet through which surgical smoke or aerosol can leave the chamber without any liquid leaving the chamber.

As shown in FIG. 8, the trap may comprise a vial 81 which may be closed with a screw cap 82 and sealed with a septum 83. A liquid transfer tube 84 may run to close to the bottom of the vial, with an arched bend 85 in order to prevent splashing and to improve the phase separation efficiency by facilitating cyclone effect. Outlet of the aerosol may occur directly underneath the inner level of the septum by a short tube 86, which may be directly connected to the mass and/or ion mobility spectrometer. PTFE frit may be used to guard against splashing at the outlet connection.

Two prototypes were built comprising a 4 ml vial and a 30 ml vial respectively, and the following parameters were measured that demonstrate their operation:

| | 4 ml version | 30 ml version |
|---|---|---|
| Delay time: | 1.8 s | 2.8 s |
| Memory effect: | 2.3 s | 5 s |
| Effective trapping volume: | 1.5-2 ml | 10-15 ml |

As can be seen, the smaller 4 ml version of the liquid trap is beneficial as it has a delay time and memory effect within the desired range. Another benefit of this embodiment is that it is inexpensive and simple, and as a consequence, disposable. The limited trapping volume can be addressed by regularly replacing the device as required.

As will be appreciated, the described embodiments of the liquid trap or separator address the requirements for the endoscopic applications without compromising the efficiency of the signal generation and the robustness of the instrument.

Analysing Sample Spectra

A list of analysis techniques which may be used in accordance with various embodiments is given in the following table:

| Analysis Techniques |
|---|
| Univariate Analysis |
| Multivariate Analysis |
| Principal Component Analysis (PCA) |
| Linear Discriminant Analysis (LDA) |
| Maximum Margin Criteria (MMC) |
| Library Based Analysis |
| Soft Independent Modelling Of Class Analogy (SIMCA) |
| Factor Analysis (FA) |
| Recursive Partitioning (Decision Trees) |
| Random Forests |
| Independent Component Analysis (ICA) |
| Partial Least Squares Discriminant Analysis (PLS-DA) |
| Orthogonal (Partial Least Squares) Projections To Latent Structures (OPLS) |
| OPLS Discriminant Analysis (OPLS-DA) |
| Support Vector Machines (SVM) |
| (Artificial) Neural Networks |
| Multilayer Perceptron |
| Radial Basis Function (RBF) Networks |
| Bayesian Analysis |

| Analysis Techniques |
| --- |
| Cluster Analysis |
| Kernelized Methods |
| Subspace Discriminant Analysis |
| K-Nearest Neighbours (KNN) |
| Quadratic Discriminant Analysis (QDA) |
| Probabilistic Principal Component Analysis (PPCA) |
| Non negative matrix factorisation |
| K-means factorisation |
| Fuzzy c-means factorisation |
| Discriminant Analysis (DA) |

Combinations of the foregoing analysis approaches can also be used, such as PCA-LDA, PCA-MMC, PLS-LDA, etc.

Analysing the sample spectra can comprise unsupervised analysis for dimensionality reduction followed by supervised analysis for classification.

By way of example, a number of different analysis techniques will now be described in more detail.

Multivariate Analysis—Developing a Model for Classification

By way of example, a method of building a classification model using multivariate analysis of plural reference sample spectra will now be described.

Figure 9:
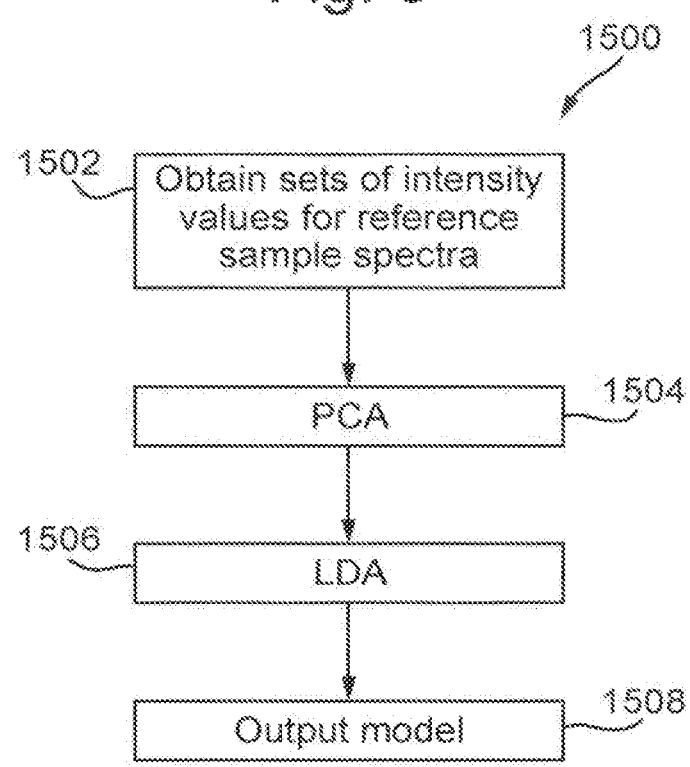
FIG. 9 shows a method of analysis that comprises building a classification model according to various embodiments.

FIG. 9 shows a method 1500 of building a classification model using multivariate analysis. In this example, the method comprises a step 1502 of obtaining plural sets of intensity values for reference sample spectra. The method then comprises a step 1504 of unsupervised principal component analysis (PCA) followed by a step 1506 of supervised linear discriminant analysis (LDA). This approach may be referred to herein as PCA-LDA. Other multivariate analysis approaches may be used, such as PCA-MMC. The PCA-LDA model is then output, for example to storage, in step 1508.

The multivariate analysis such as this can provide a classification model that allows a sample (such as an aerosol, smoke or vapour sample, a biological sample, etc.) to be classified using one or more sample spectra obtained from the sample. The multivariate analysis will now be described in more detail with reference to a simple example.

Figure 10:
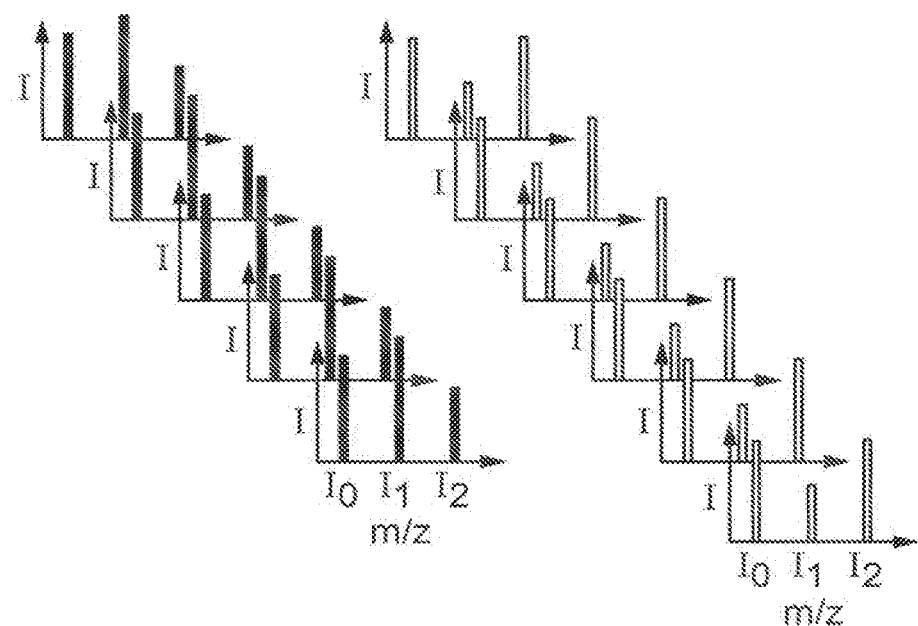
FIG. 10 shows a set of reference sample spectra obtained from two classes of known reference samples.

FIG. 10 shows a set of reference sample spectra obtained from two classes of known reference samples. The classes may be any one or more of the classes of target described herein. However, for simplicity, in this example the two classes will be referred as a left-hand class and a right-hand class.

Each of the reference sample spectra has been pre-processed in order to derive a set of three reference peak-intensity values for respective mass to charge ratios in that reference sample spectrum. Although only three reference peak-intensity values are shown, it will be appreciated that many more reference peak-intensity values (e.g., ~100 reference peak-intensity values) may be derived for a corresponding number of mass to charge ratios in each of the reference sample spectra. In other embodiments, the reference peak-intensity values may correspond to: masses; mass to charge ratios; ion mobilities (drift times); and/or operational parameters.

Figure 11:
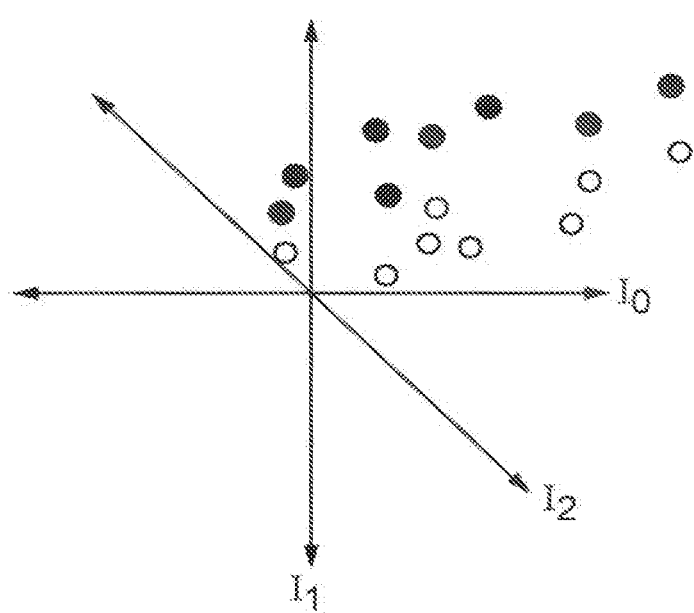
FIG. 11 shows a multivariate space having three dimensions defined by intensity axes, wherein the multivariate space comprises plural reference points, each reference point corresponding to a set of three peak intensity values derived from a reference sample spectrum.

FIG. 11 shows a multivariate space having three dimensions defined by intensity axes. Each of the dimensions or intensity axes corresponds to the peak-intensity at a particular mass to charge ratio. Again, it will be appreciated that there may be many more dimensions or intensity axes (e.g., ~100 dimensions or intensity axes) in the multivariate space. The multivariate space comprises plural reference points, with each reference point corresponding to a reference sample spectrum, i.e., the peak-intensity values of each reference sample spectrum provide the co-ordinates for the reference points in the multivariate space.

The set of reference sample spectra may be represented by a reference matrix D having rows associated with respective reference sample spectra, columns associated with respective mass to charge ratios, and the elements of the matrix being the peak-intensity values for the respective mass to charge ratios of the respective reference sample spectra.

In many cases, the large number of dimensions in the multivariate space and matrix D can make it difficult to group the reference sample spectra into classes. PCA may accordingly be carried out on the matrix D in order to calculate a PCA model that defines a PCA space having a reduced number of one or more dimensions defined by principal component axes. The principal components may be selected to be those that comprise or "explain" the largest variance in the matrix D and that cumulatively explain a threshold amount of the variance in the matrix D.

Figure 12:
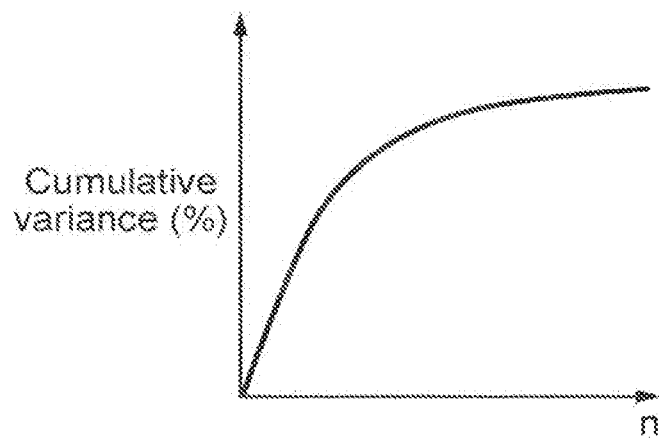
FIG. 12 shows a general relationship between cumulative variance and number of components of a PCA model.

FIG. 12 shows how the cumulative variance may increase as a function of the number n of principal components in the PCA model. The threshold amount of the variance may be selected as desired.

The PCA model may be calculated from the matrix D using a non-linear iterative partial least squares (NIPALS) algorithm or singular value decomposition, the details of which are known to the skilled person and so will not be described herein in detail. Other methods of calculating the PCA model may be used.

The resultant PCA model may be defined by a PCA scores matrix S and a PCA loadings matrix L. The PCA may also produce an error matrix E, which contains the variance not explained by the PCA model. The relationship between D, S, L and E may be:

$$D = SL^T + E \quad (1)$$

Figure 13:
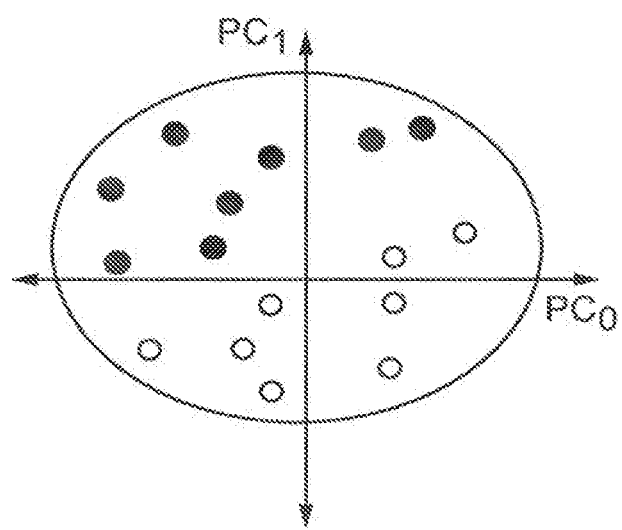
FIG. 13 shows a PCA space having two dimensions defined by principal component axes, wherein the PCA space comprises plural transformed reference points or scores, each transformed reference point or score corresponding to a reference point of FIG. 11.

FIG. 13 shows the resultant PCA space for the reference sample spectra of FIGS. 10 and 11. In this example, the PCA model has two principal components $PC_0$ and $PC_1$ and the PCA space therefore has two dimensions defined by two principal component axes. However, a lesser or greater number of principal components may be included in the PCA model as desired. It is generally desired that the number of principal components is at least one less than the number of dimensions in the multivariate space.

The PCA space comprises plural transformed reference points or PCA scores, with each transformed reference point or PCA score corresponding to a reference sample spectrum of FIG. 10 and therefore to a reference point of FIG. 11.

As is shown in FIG. 13, the reduced dimensionality of the PCA space makes it easier to group the reference sample spectra into the two classes. Any outliers may also be identified and removed from the classification model at this stage.

Further supervised multivariate analysis, such as multi-class LDA or maximum margin criteria (MMC), using the PCA space may then be performed so as to define classes and, optionally, further reduce the dimensionality.

As will be appreciated by the skilled person, multi-class LDA seeks to maximise the ratio of the variance between classes to the variance within classes (i.e., so as to give the largest possible distance between the most compact classes possible). The details of LDA are known to the skilled person and so will not be described herein in detail.

The resultant PCA-LDA model may be defined by a transformation matrix U, which may be derived from the PCA scores matrix S and class assignments for each of the transformed spectra contained therein by solving a generalised eigenvalue problem.

The transformation of the scores S from the original PCA space into the new LDA space may then be given by:

$$Z = SU \qquad (2)$$

where the matrix Z contains the scores transformed into the LDA space.

Figure 14:
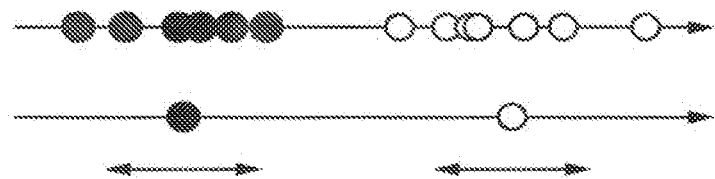
FIG. 14 shows a PCA-LDA space having a single dimension or axis, wherein the LDA is performed based on the PCA space of FIG. 13, the PCA-LDA space comprising plural further transformed reference points or class scores, each further transformed reference point or class score corresponding to a transformed reference point or score of FIG. 13.

FIG. 14 shows a PCA-LDA space having a single dimension or axis, wherein the LDA is performed in the PCA space of FIG. 13. As is shown in FIG. 14, the LDA space comprises plural further transformed reference points or PCA-LDA scores, with each further transformed reference point corresponding to a transformed reference point or PCA score of FIG. 13. In this example, the further reduced dimensionality of the PCA-LDA space makes it even easier to group the reference sample spectra into the two classes. Each class in the PCA-LDA model may be defined by its transformed class average and covariance matrix or one or more hyperplanes (including points, lines, planes or higher order hyperplanes) or hypersurfaces or Voronoi cells in the PCA-LDA space.

The PCA loadings matrix L, the LDA matrix U and transformed class averages and covariance matrices or hyperplanes or hypersurfaces or Voronoi cells may be output to a database for later use in classifying an aerosol, smoke or vapour sample.

The transformed covariance matrix in the LDA space $V'_g$ for class g may be given by $$V'_g = U^T V_g U \qquad (3)$$

where $V_g$ are the class covariance matrices in the PCA space.

The transformed class average position $z_g$ for class g may be given by $$s_g U = z_g \qquad (4)$$

where $s_g$ is the class average position in the PCA space.

Multivariate Analysis—Using a Model for Classification

By way of example, a method of using a classification model to classify a sample (such as an aerosol, smoke or vapour sample) will now be described.

Figure 15:
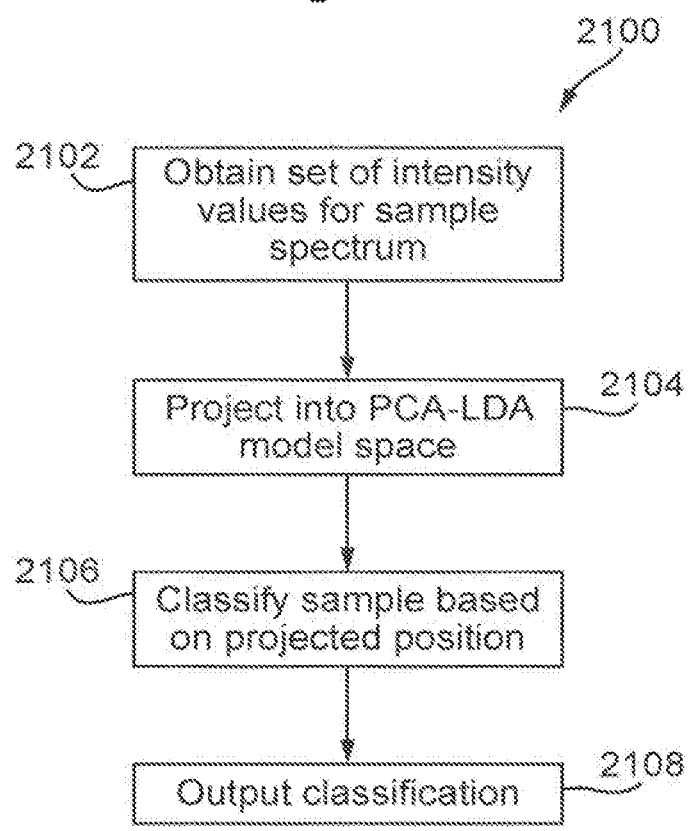
FIG. 15 shows a method of analysis that comprises using a classification model according to various embodiments.

FIG. 15 shows a method 2100 of using a classification model. In this example, the method comprises a step 2102 of obtaining a set of intensity values for a sample spectrum. The method then comprises a step 2104 of projecting the set of intensity values for the sample spectrum into PCA-LDA model space. Other classification model spaces may be used, such as PCA-MMC. The sample spectrum is then classified at step 2106 based on the project position and the classification is then output in step 2108.

Classification of a sample (e.g. an aerosol, smoke or vapour sample) will now be described in more detail with reference to the simple PCA-LDA model described above.

Figure 16:
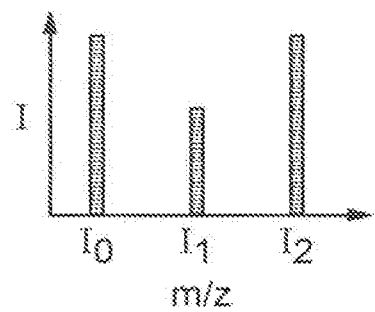
FIG. 16 shows a sample spectrum obtained from an unknown sample.

FIG. 16 shows a sample spectrum obtained from an unknown aerosol, smoke or vapour sample. The sample spectrum has been pre-processed in order to derive a set of three sample peak-intensity values for respective mass to charge ratios. As mentioned above, although only three sample peak-intensity values are shown, it will be appreciated that many more sample peak-intensity values (e.g., ~100 sample peak-intensity values) may be derived at many more corresponding mass to charge ratios for the sample spectrum. Also, as mentioned above, in other embodiments, the sample peak-intensity values may correspond to: masses; mass to charge ratios; ion mobilities (drift times); and/or operational parameters.

The sample spectrum may be represented by a sample vector $d_x$, with the elements of the vector being the peak-intensity values for the respective mass to charge ratios. A transformed PCA vector $s_x$ for the sample spectrum can be obtained as follows:

$$d_x L = s_x \qquad (5)$$

Then, a transformed PCA-LDA vector $z_x$ for the sample spectrum can be obtained as follows:

$$s_x U = z_x \qquad (6)$$

Figure 17:
FIG. 17 shows the PCA-LDA space of FIG. 14, wherein the PCA-LDA space further comprises a PCA-LDA projected sample point derived from the peak intensity values of the sample spectrum of FIG. 16.

FIG. 17 again shows the PCA-LDA space of FIG. 14. However, the PCA-LDA space of FIG. 17 further comprises the projected sample point, corresponding to the transformed PCA-LDA vector $z_x$, derived from the peak intensity values of the sample spectrum of FIG. 16.

In this example, the projected sample point is to one side of a hyperplane between the classes that relates to the right-hand class, and so the sample (aerosol, smoke or vapour sample) may be classified as belonging to the right-hand class.

Alternatively, the Mahalanobis distance from the class centres in the LDA space may be used, where the Mahalanobis distance of the point $z_x$ from the centre of class g may be given by the square root of:

$$(z_x - z_g)^T (V'_g)^{-1} (z_x - z_g) \qquad (8)$$

and the data vector $d_x$ may be assigned to the class for which this distance is smallest.

In addition, treating each class as a multivariate Gaussian, a probability of membership of the data vector to each class may be calculated.

Library Based Analysis—Developing a Library for Classification

By way of example, a method of building a classification library using plural input reference sample spectra will now be described.

Figure 18:
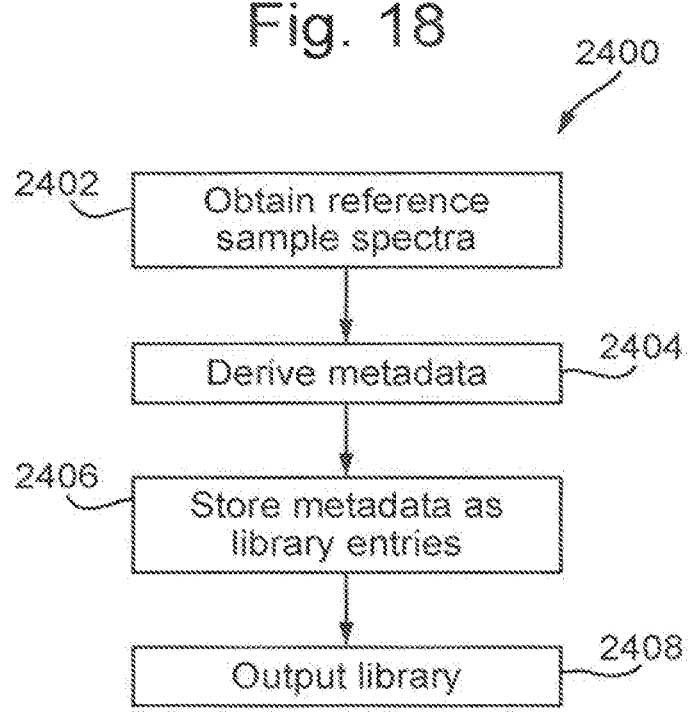
FIG. 18 shows a method of analysis that comprises building a classification library according to various embodiments.

FIG. 18 shows a method 2400 of building a classification library. In this example, the method comprises a step 2402 of obtaining plural input reference sample spectra and a step 2404 of deriving metadata from the plural input reference sample spectra for each class of sample. The method then comprises a step 2404 of storing the metadata for each class of sample as a separate library entry. The classification library is then output, for example to electronic storage, in step 2406.

A classification library such as this allows a sample (e.g. an aerosol, smoke or vapour sample) to be classified using one or more sample spectra obtained from the sample. The library based analysis will now be described in more detail with reference to an example.

In this example, each entry in the classification library is created from plural pre-processed reference sample spectra that are representative of a class. In this example, the reference sample spectra for a class are pre-processed according to the following procedure:

First, a re-binning process is performed. In this embodiment, the data are resampled onto a logarithmic grid with abscissae:

$$x_i = \left\lfloor N_{chan} \log \frac{m}{M_{min}} \bigg/ \log \frac{M_{max}}{M_{min}} \right\rfloor \qquad (7)$$

where $N_{chan}$ is a selected value and $\lfloor x \rfloor$ denotes the nearest integer below x. In one example, $N_{chan}$ is $2^{12}$ or 4096.

Then, a background subtraction process is performed. In this embodiment, a cubic spline with k knots is then constructed such that p % of the data between each pair of knots lies below the curve. This curve is then subtracted from the data. In one example, k is 32. In one example, p is 5.

A constant value corresponding to the q % quantile of the intensity subtracted data is then subtracted from each intensity. Positive and negative values are retained. In one example, q is 45.

Then, a normalisation process is performed. In this embodiment, the data are normalised to have mean $\bar{y}_i$. In one example, $\bar{y}_i=1$.

An entry in the library then consists of metadata in the form of a median spectrum value $\mu_i$ and a deviation value $D_i$ for each of the $N_{chan}$ points in the spectrum.

The likelihood for the i'th channel is given by:

$$Pr(y_i | \mu_i, D_i) = \frac{1}{D_i} \frac{C^{C-1/2}\Gamma(C)}{\sqrt{\pi}\,\Gamma(C-1/2)} \frac{1}{\left(C + \frac{(y_i - \mu_i)^2}{D_i^2}\right)^C} \quad (8)$$

where $\frac{1}{2} \leq C < \infty$ and where $\Gamma(C)$ is the gamma function.

The above equation is a generalised Cauchy distribution which reduces to a standard Cauchy distribution for C=1 and becomes a Gaussian (normal) distribution as $C \to \infty$. The parameter $D_i$ controls the width of the distribution (in the Gaussian limit $D_i = \sigma_i$ is simply the standard deviation) while the global value C controls the size of the tails.

In one example, C is 3/2, which lies between Cauchy and Gaussian, so that the likelihood becomes:

$$Pr(y_i | \mu_i, D_i) = \frac{3}{4} \frac{1}{D_i} \frac{1}{(3/2 + (y_i - \mu_i)^2 / D_i^2)^{3/2}} \quad (9)$$

For each library entry, the parameters $\mu_i$ are set to the median of the list of values in the i'th channel of the input reference sample spectra while the deviation $D_i$ is taken to be the interquartile range of these values divided by $\sqrt{2}$. This choice can ensure that the likelihood for the i'th channel has the same interquartile range as the input data, with the use of quantiles providing some protection against outlying data.

Library Based Analysis—Using a Library for Classification

By way of example, a method of using a classification library to classify a sample (e.g. an aerosol, smoke or vapour sample) will now be described.

Figure 19:
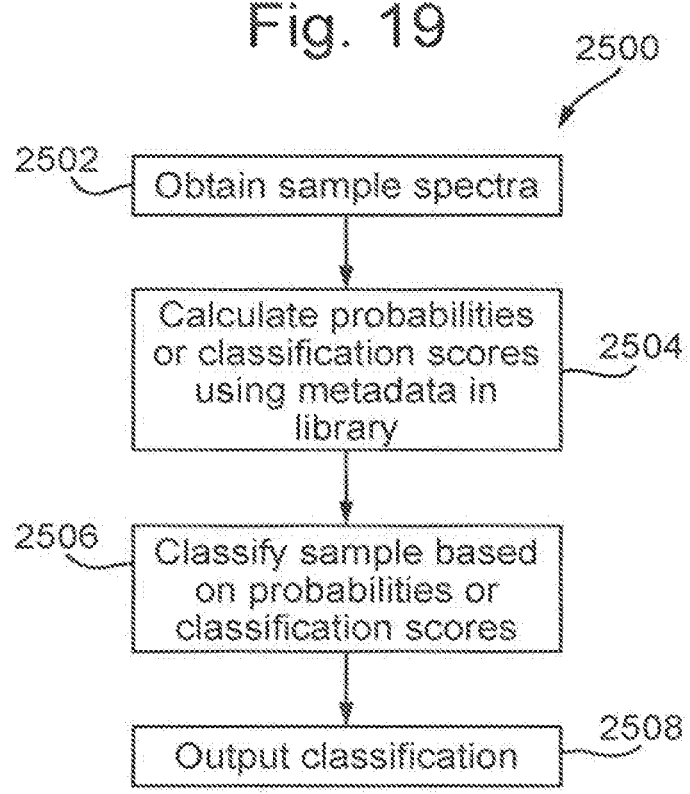
FIG. 19 shows a method of analysis that comprises using a classification library according to various embodiments.

FIG. 19 shows a method 2500 of using a classification library. In this example, the method comprises a step 2502 of obtaining a set of plural sample spectra. The method then comprises a step 2504 of calculating a probability or classification score for the set of plural sample spectra for each class of sample using metadata for the class entry in the classification library. The sample spectra are then classified at step 2506 and the classification is then output in step 2508.

Classification of a sample (e.g. an aerosol, smoke or vapour sample) will now be described in more detail with reference to the classification library described above.

In this example, an unknown sample spectrum y is the median spectrum of a set of plural sample spectra. Taking the median spectrum y can protect against outlying data on a channel by channel basis.

The likelihood $L_s$ for the input data given the library entry s is then given by:

$$L_s = Pr(y | \mu, D) = \prod_{i=1}^{N_{chan}} Pr(y_i | \mu_i, D_i) \quad (10)$$

wherein $\mu_i$ and $D_i$ are, respectively, the library median values and deviation values for channel i. The likelihoods $L_s$ may be calculated as log likelihoods for numerical safety.

The likelihoods $L_s$ are then normalised over all candidate classes 's' to give probabilities, assuming a uniform prior probability over the classes. The resulting probability for the class $\tilde{s}$ is given by:

$$Pr(\tilde{s} | y) = \frac{L_{\tilde{s}}^{(1/F)}}{\sum_s L_s^{(1/F)}} \quad (11)$$

The exponent (1/F) can soften the probabilities which may otherwise be too definitive. In one example, F=100. These probabilities may be expressed as percentages, e.g., in a user interface.

Alternatively, RMS classification scores $R_s$ may be calculated using the same median sample values and derivation values from the library:

$$R_s(y, \mu, D) = \sqrt{\frac{1}{N_{chan}} \sum_{i=1}^{N_{chan}} \frac{(y_i - \mu_i)^2}{D_i^2}} \quad (12)$$

Again, the scores $R_s$ are normalised over all candidate classes 's'.

The sample (e.g. aerosol, smoke or vapour sampl)e may then be classified as belonging to the class having the highest probability and/or highest RMS classification score.

Methods of Medical Treatment, Surgery and Diagnosis and Non-Medical Methods

Various different embodiments are contemplated. According to some embodiments the methods disclosed above may be performed on in vivo, ex vivo or in vitro tissue. The tissue may comprise human or non-human animal tissue.

Various embodiments are contemplated wherein analyte ions generated by an ambient ionisation ion source are then subjected either to: (i) mass analysis by a mass analyser or filter such as a quadrupole mass analyser or a Time of Flight mass analyser; (ii) ion mobility analysis (IMS) and/or differential ion mobility analysis (DMA) and/or Field Asymmetric Ion Mobility Spectrometry (FAIMS) analysis; and/or (iii) a combination of firstly (or vice versa) ion mobility analysis (IMS) and/or differential ion mobility analysis (DMA) and/or Field Asymmetric Ion Mobility Spectrometry (FAIMS) analysis followed by secondly (or vice versa) mass analysis by a mass analyser or filter such as a quadrupole mass analyser or a Time of Flight mass analyser. Various embodiments also relate to an ion mobility spectrometer and/or mass analyser and a method of ion mobility spectrometry and/or method of mass analysis. Ion mobility analysis may be performed prior to mass to charge ratio analysis or vice versa.

Various references are made in the present application to mass analysis, mass analysers, mass analysing, mass spectrometric data, mass spectrometers and other related terms referring to apparatus and methods for determining the mass or mass to charge of analyte ions. It should be understood that it is equally contemplated that the present invention may extend to ion mobility analysis, ion mobility analysers, ion mobility analysing, ion mobility data, ion mobility spectrometers, ion mobility separators and other related terms referring to apparatus and methods for determining the ion mobility, differential ion mobility, collision cross section or interaction cross section of analyte ions. Furthermore, it should also be understood that embodiments are contemplated wherein analyte ions may be subjected to a combination of both ion mobility analysis and mass analysis i.e. that both (a) the ion mobility, differential ion mobility, collision cross section or interaction cross section of analyte ions together with (b) the mass to charge of analyte ions is determined. Accordingly, hybrid ion mobility-mass spectrometry (IMS-MS) and mass spectrometry-ion mobility (MS-IMS) embodiments are contemplated wherein both the ion mobility and mass to charge ratio of analyte ions generated e.g. by an ambient ionisation ion source are determined. Ion mobility analysis may be performed prior to mass to charge ratio analysis or vice versa. Furthermore, it should be understood that embodiments are contemplated wherein references to mass spectrometric data and databases comprising mass spectrometric data should also be understood as encompassing ion mobility data and differential ion mobility data etc. and databases comprising ion mobility data and differential ion mobility data etc. (either in isolation or in combination with mass spectrometric data).

Various surgical, therapeutic, medical treatment and diagnostic methods are contemplated.

However, other embodiments are contemplated which relate to non-surgical and non-therapeutic methods of mass spectrometry and/or ion mobility spectrometry which are not performed on in vivo tissue. Other related embodiments are contemplated which are performed in an extracorporeal manner such that they are performed outside of the human or animal body.

Further embodiments are contemplated wherein the methods are performed on a non-living human or animal, for example, as part of an autopsy procedure.

It has also been recognised that a tool comprising a relatively extended and miniaturised probe comprising an ambient ion source for generating aerosol, smoke or vapour from a sample, i.e. similarly to the endoscope described above, may find application outside of the surgical or medical environments.

For instance, such a tool may be used for minimally invasive analysis of fully packed containers e.g. at customs or airport security. The tool may be inserted into a relatively small hole formed in the container, with the ambient ion source then deployed through the tool deployment opening and activated to generate gaseous, smoke or vapour analyte material from within the container, with the gaseous, smoke or vapour material then being aspirated through fenestrations in the tool tubing and transported to an analyser for mass and/or ion mobility spectrometric analysis.

Similarly, such a tool may find applications for analysis of closed pipe heating or cooling systems. It is known that organic growth such as fungi, bacteria, biofilms and/or algae may clog the heating or cooling pipes, but it is generally difficult to identify the organic material within such systems and hence difficult to ascertain how to treat it. This can be a particular problem in the cooling systems of a nuclear reactor, where disassembly of the cooling system for cleaning is prohibitively time consuming and expensive. By passing the tool through the pipework and deploying the ambient ion source into contact with the obstruction to generate gaseous, smoke or vapour analyte material which can then be aspirated into the tool housing and transported to a mass and/or ion mobility spectrometer for analysis, it may be possible to identify the nature of the organic growth and hence help determine how best to remove it.

In the same manner, such a tool may find application in the fields of pest/parasite control, or structural testing/surveying. For instance, current methods for analysing fungal growth in the foundations or walls of a house tend to rely on optical imaging methods which can be inconclusive. By probing the growth and then mass analysing and/or ion mobility analysing the generated gaseous, smoke or vapour analyte material it is possible to more accurately determine the nature of the fungal growth.

Although the has been described with reference to preferred embodiments, it will be understood by those skilled in the art that various changes in form and detail may be made without departing from the scope of the invention as set forth in the accompanying claims.

The invention claimed is:

1. An apparatus for mass spectrometry and/or ion mobility spectroscopy comprising:
a first device arranged and adapted to generate aerosol, smoke or vapour from a target,
wherein said first device comprises one or more electrodes, and wherein said first device is arranged and adapted to generate said aerosol, smoke or vapour from said target by contacting said target with said one or more electrodes;
a device arranged and adapted to apply an AC or RF voltage to said one or more electrodes in order to generate said aerosol, smoke or vapour;
one or more second devices arranged and adapted to aspirate aerosol, smoke or vapour and/or liquid to or towards a mass and/or ion mobility analyser; and
a liquid trap or separator located between said first device and said mass and/or ion mobility analyser, wherein said liquid trap or separator is arranged and adapted to capture and/or discard liquid aspirated by said one or more second devices.

2. An apparatus for mass spectrometry and/or ion mobility spectroscopy comprising:
a first device arranged and adapted to generate aerosol, smoke or vapour from a target, wherein said first device comprises one or more electrodes, wherein said one or more electrodes comprises either: (i) a monopolar device; (ii) a bipolar device; or (iii) a multi-phase RF device, and wherein said first device is arranged and adapted to generate said aerosol, smoke or vapour from said target by contacting said target with said one or more electrodes;
one or more second devices arranged and adapted to aspirate aerosol, smoke or vapour and/or liquid to or towards a mass and/or ion mobility analyser; and
a liquid trap or separator located between said first device and said mass and/or ion mobility analyser, wherein said liquid trap or separator is arranged and adapted to capture and/or discard liquid aspirated by said one or more second devices.

3. The apparatus as claimed in claim 1, wherein said target comprises native or unmodified target material.

4. The apparatus as claimed in claim 1, wherein said target comprises biological tissue, biological matter, a bacterial colony or a fungal colony.

5. The apparatus as claimed in claim 4, wherein said biological tissue comprises in vivo biological tissue.

6. The apparatus as claimed in claim 4, wherein said biological tissue comprises adrenal gland tissue, appendix tissue, bladder tissue, bone, bowel tissue, brain tissue, breast tissue, bronchi, coronal tissue, ear tissue, oesophagus tissue, eye tissue, gall bladder tissue, genital tissue, heart tissue, hypothalamus tissue, kidney tissue, large intestine tissue, intestinal tissue, larynx tissue, liver tissue, lung tissue, lymph nodes, mouth tissue, nose tissue, pancreatic tissue, parathyroid gland tissue, pituitary gland tissue, prostate tissue, rectal tissue, salivary gland tissue, skeletal muscle tissue, skin tissue, small intestine tissue, spinal cord, spleen tissue, stomach tissue, thymus gland tissue, trachea tissue, thyroid tissue, ureter tissue, urethra tissue, soft and connective tissue, peritoneal tissue, blood vessel tissue and/or fat tissue; (ii) grade I, grade II, grade III or grade IV cancerous tissue; (iii) metastatic cancerous tissue; (iv) mixed grade cancerous tissue; (v) a sub-grade cancerous tissue; (vi) healthy or normal tissue; or (vii) cancerous or abnormal tissue.

7. The apparatus as claimed in claim 1, wherein said liquid trap or separator comprises one or more porous and/or absorbent materials arranged and adapted to absorb and/or capture and/or discard aspirated liquid.

8. An apparatus as claimed in claim 1, for mass spectrometry and/or ion mobility spectrometry comprising:
   a first device arranged and adapted to generate aerosol, smoke or vapour from a target;
   a mass and/or ion mobility analyser;
   one or more second devices arranged and adapted to aspirate aerosol, smoke or vapour and/or liquid to or towards the analyser; and
   a liquid trap or separator located between said first device and said mass and/or ion mobility analyser, wherein said liquid trap or separator comprises a centrifugal liquid separator, and wherein said liquid trap or separator is arranged and adapted to capture and/or discard liquid aspirated by said one or more second devices.

9. The apparatus as claimed in claim 1, wherein said liquid trap or separator comprises a sealed chamber comprising an inlet, wherein said liquid trap or separator is arranged and adapted such that in use said aerosol, smoke or vapour and/or liquid is introduced into said chamber though said inlet, wherein said sealed chamber further comprises an outlet, wherein said liquid trap or separator is arranged and adapted such that in use aerosol, smoke and/or vapour can leave said chamber through said outlet substantially without liquid leaving said chamber, and wherein in use an exit of said inlet is located below an entrance of said outlet.

10. The apparatus as claimed in claim 1, wherein said liquid comprises water, saliva, digestive fluids, chyme, saline, blood, urine, mucus and/or one or more other bodily fluids.

11. The apparatus as claimed in claim 1, further comprising an ionisation device arranged and adapted to ionise said aerosol, smoke and/or vapour to form analyte ions, wherein said ionisation device comprises a collision surface located within a vacuum chamber, and wherein said apparatus is arranged and adapted to cause at least some of said aerosol, smoke and/or vapour to impact upon said collision surface in order to form said analyte ions.

12. The apparatus as claimed in claim 1, further comprising a device which is arranged and adapted to provide real time and/or delayed information to a user of said first device,
   wherein said information comprises mass and/or ion mobility spectral information and/or tissue classification information.

13. An apparatus, for mass spectrometry and/or ion mobility spectrometry comprising:
   a first device arranged and adapted to generate aerosol, smoke or vapour from a target;
   a mass and/or ion mobility analyser;
   one or more second devices arranged and adapted to aspirate aerosol, smoke or vapour and/or liquid to or towards the analyser;
   a liquid trap or separator located between said first device and said mass and/or ion mobility analyser, wherein said liquid trap or separator is arranged and adapted to capture and/or discard liquid aspirated by said one or more second devices; and
   a device which is arranged and adapted to generate feedback
and/or an alarm and/or an alert to a user of said first device when tissue or other matter from an undesired target region or area is being analysed.

14. A method of mass spectrometry and/or ion mobility spectrometry comprising:
   generating aerosol, smoke or vapour from a target using a first device,
      wherein said first device comprises one or more electrodes, and wherein said first device is arranged and adapted to generate said aerosol, smoke or vapour from said target by contacting said target with said one or more electrodes;
   applying an AC or RF voltage to said one or more electrodes in order to generate said aerosol, smoke or vapour;
   aspirating aerosol, smoke or vapour and/or liquid to or towards a mass and/or ion mobility analyser; and
   capturing and/or discarding aspirated liquid using a liquid trap or separator located between said first device and said mass and/or ion mobility analyser.

15. An electrosurgical apparatus comprising:
   a first device arranged and adapted to generate aerosol, smoke or vapour from a target,
   wherein said first device comprises one or more electrodes, and wherein said first device is arranged and adapted to generate said aerosol, smoke or vapour from said target by contacting said target with said one or more electrodes;
   a device arranged and adapted to activate said first device when said first device is in contact, in use, with biological tissue so as to generate aerosol, smoke or vapour;
   a device arranged and adapted to apply an AC or RF voltage to said one or more electrodes in order to said generate aerosol, smoke or vapour;
   a device arranged and adapted to aspirate aerosol, smoke, vapour and/or liquid;
   a device arranged and adapted to capture and/or discard aspirated liquid; and
   a mass and/or ion mobility spectrometer comprising: (i) a collision surface located within a vacuum chamber of said mass and/or ion mobility spectrometer wherein, in use, remaining aerosol, smoke and/or vapour is arranged to impact upon said collision surface so as to form analyte ions; and (ii) an analyser for analysing said analyte ions.

16. A mass and/or ion mobility spectrometer comprising an apparatus as claimed in claim 1.

17. The apparatus as claimed in claim 1, wherein said one or more second
devices are arranged and adapted to aspirate said aerosol, smoke or vapour generated by said first device to or towards the analyser, and wherein said one or more second devices are further arranged and adapted to aspirate liquid that is other than generated from said target to or towards the analyser.

18. The apparatus as claimed in claim 1, wherein said one or more second devices are arranged and adapted to aspirate said aerosol, smoke or vapour generated by said first device to or towards the analyser, and wherein said one or more second devices are further arranged and adapted to aspirate liquid that is other than generated by said first device to or towards the analyser.

* * * * *